(12) United States Patent
Tsunoda

(10) Patent No.: US 12,121,427 B2
(45) Date of Patent: Oct. 22, 2024

(54) DISPOSABLE WEARABLE ARTICLE

(71) Applicant: Daio Paper Corporation, Ehime (JP)

(72) Inventor: Arika Tsunoda, Tochigi (JP)

(73) Assignee: Daio Paper Corporation, Ehime (JP)

( * ) Notice: Subject to any disclaimer, the term of this patent is extended or adjusted under 35 U.S.C. 154(b) by 992 days.

(21) Appl. No.: 17/051,529

(22) PCT Filed: May 24, 2019

(86) PCT No.: PCT/JP2019/020582
§ 371 (c)(1),
(2) Date: Oct. 29, 2020

(87) PCT Pub. No.: WO2019/235244
PCT Pub. Date: Dec. 12, 2019

(65) Prior Publication Data
US 2021/0228424 A1      Jul. 29, 2021

(30) Foreign Application Priority Data

Jun. 4, 2018    (JP) ................................. 2018-106829

(51) Int. Cl.
*A61F 13/15*      (2006.01)
*A61F 13/49*      (2006.01)
(Continued)

(52) U.S. Cl.
CPC ........ *A61F 13/4902* (2013.01); *A61F 13/496* (2013.01); *A61F 13/84* (2013.01);
(Continued)

(58) Field of Classification Search
CPC ............ A61F 2013/8497; A61F 13/496; A61F 13/49015; A61F 13/84; A61F 13/4902; A61F 2013/49022
See application file for complete search history.

(56) References Cited

U.S. PATENT DOCUMENTS

| 6,572,595 | B1 * | 6/2003 | Klemp ................ A61F 13/4942 604/385.24 |
| 2006/0254698 | A1 * | 11/2006 | Tachibana ......... A61F 13/15593 156/155 |
| 2015/0056424 | A1 * | 2/2015 | Muslet ............. A61F 13/51464 156/244.11 |

FOREIGN PATENT DOCUMENTS

| EP | 3421021 A1 * | 1/2019 | ....... A61F 13/15699 |
| JP | 2015-514521 | 5/2015 | |

(Continued)

OTHER PUBLICATIONS

International Search Report for PCT/JP2019/020582, mailed Aug. 20, 2019.

*Primary Examiner* — Jacqueline F Stephens
(74) *Attorney, Agent, or Firm* — Andrus Intellectual Property Law, LLP

(57) ABSTRACT

A disposable wearable article has an elastic sheet stretchable structure in which a first and second sheet layer are bonded through joint holes penetrating an elastic sheet at a plurality of bonded portions arranged at intervals, wherein a part of the elastic sheet located in a stretchable region is printed with a first design, a part of the elastic sheet in the non-stretchable region is printed with a second design, the first design and the second design are the same when the stretchable and non-stretchable region are at an elongation at elastic limit, and a stretchable direction dimension of design elements of the first design when a stretch rate of the stretchable region is 130% or more is 80% or more of a stretchable direction dimension of design elements of the first design when the stretchable region is at the elongation at elastic limit.

6 Claims, 30 Drawing Sheets

(51) Int. Cl.
*A61F 13/496* (2006.01)
*A61F 13/84* (2006.01)

(52) U.S. Cl.
CPC .............. *A61F 2013/49022* (2013.01); *A61F 2013/8497* (2013.01)

(56) References Cited

FOREIGN PATENT DOCUMENTS

| | | | | |
|---|---|---|---|---|
| JP | 2015-204982 | 11/2015 | | |
| JP | 5918877 | 5/2016 | | |
| JP | 5967736 | 8/2016 | | |
| JP | 5980355 | 8/2016 | | |
| JP | 5980367 | 8/2016 | | |
| JP | 6049228 | 12/2016 | | |
| JP | 2017-35412 | 2/2017 | | |
| JP | 2017-148169 | 8/2017 | | |
| WO | WO-2013159273 A1 * | 10/2013 | ........ | A61F 13/49011 |
| WO | WO-2017145776 A1 * | 8/2017 | ....... | A61F 13/15699 |

* cited by examiner

[FIG.1]
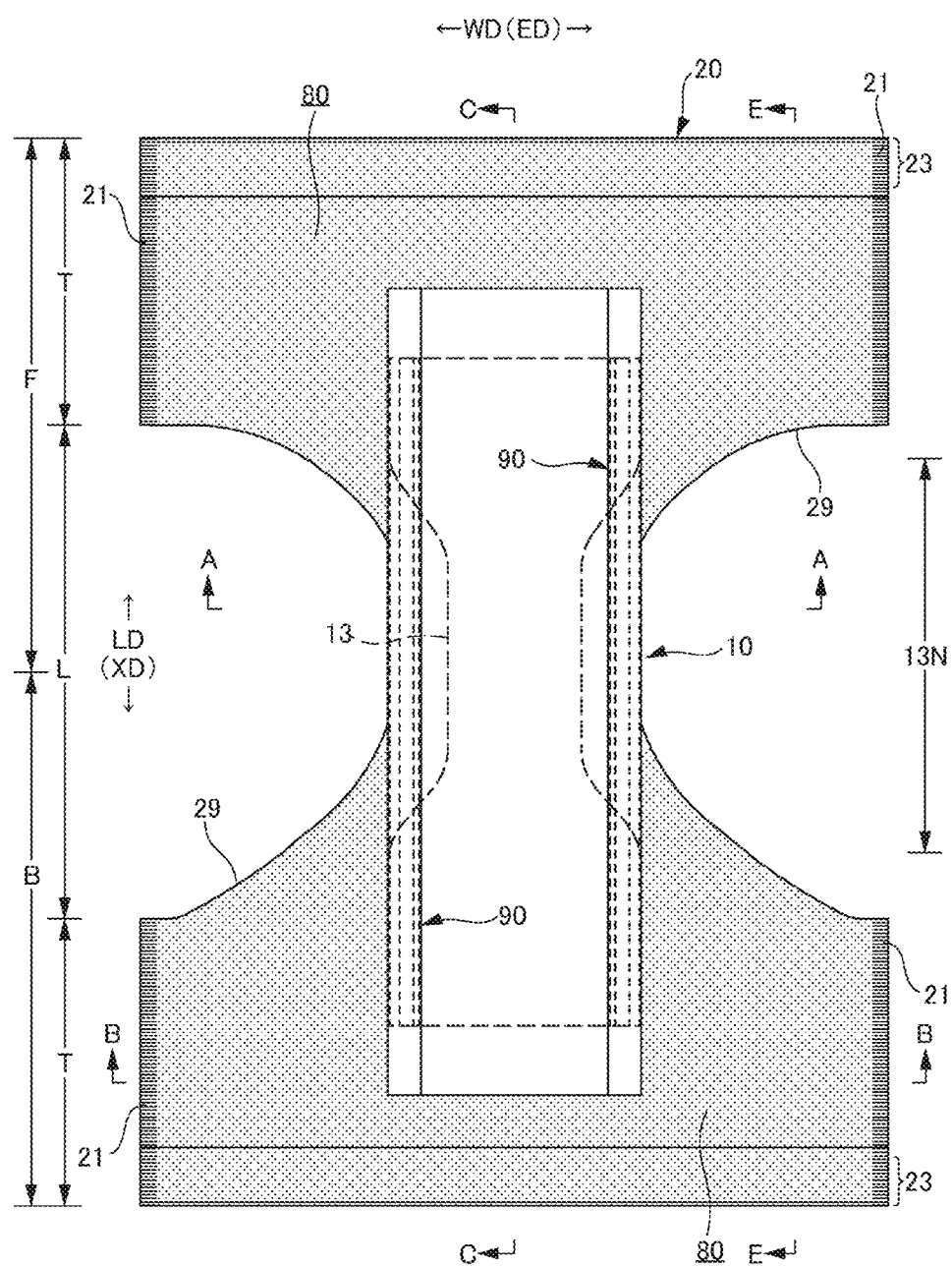

[FIG.2]
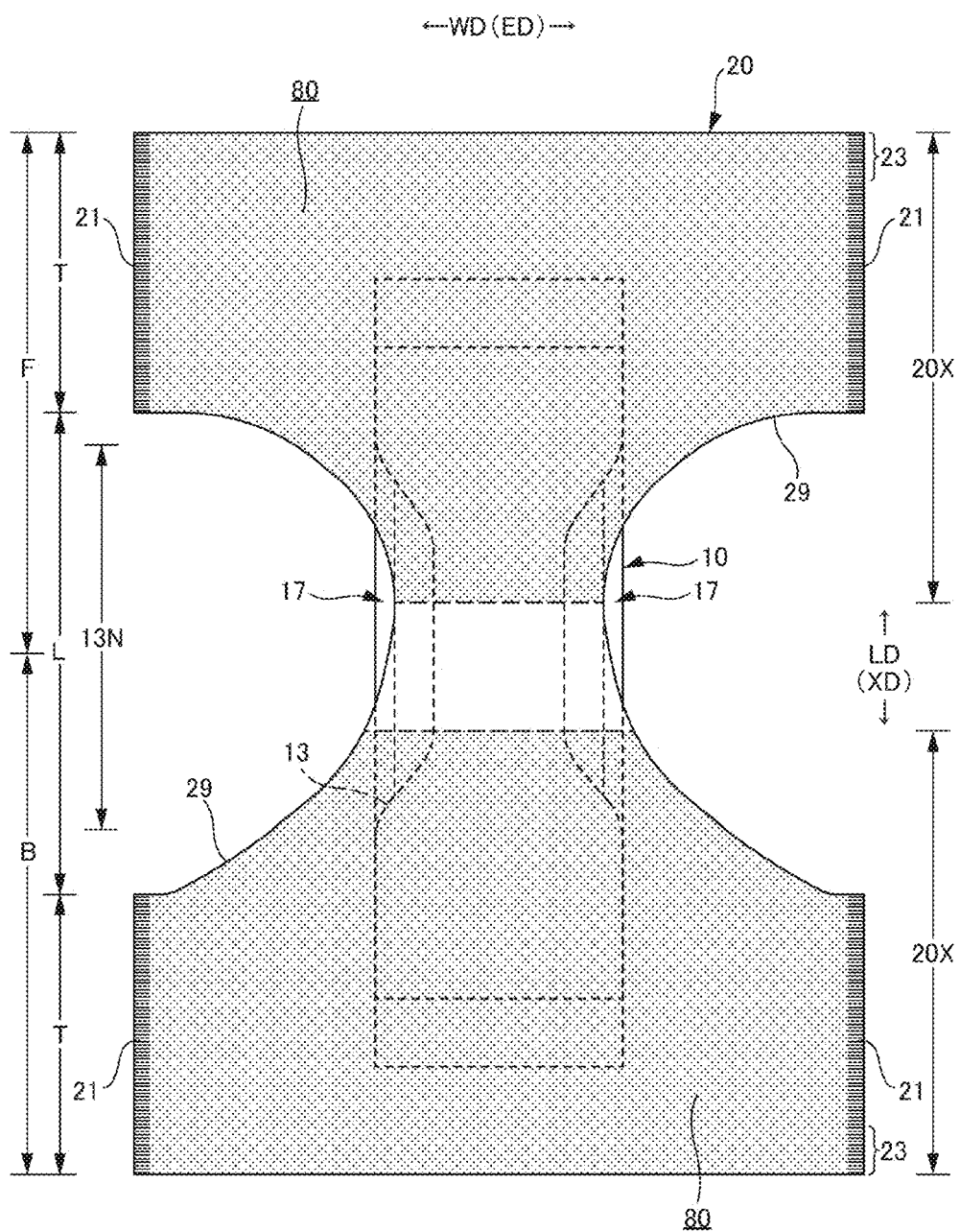

[FIG.3]
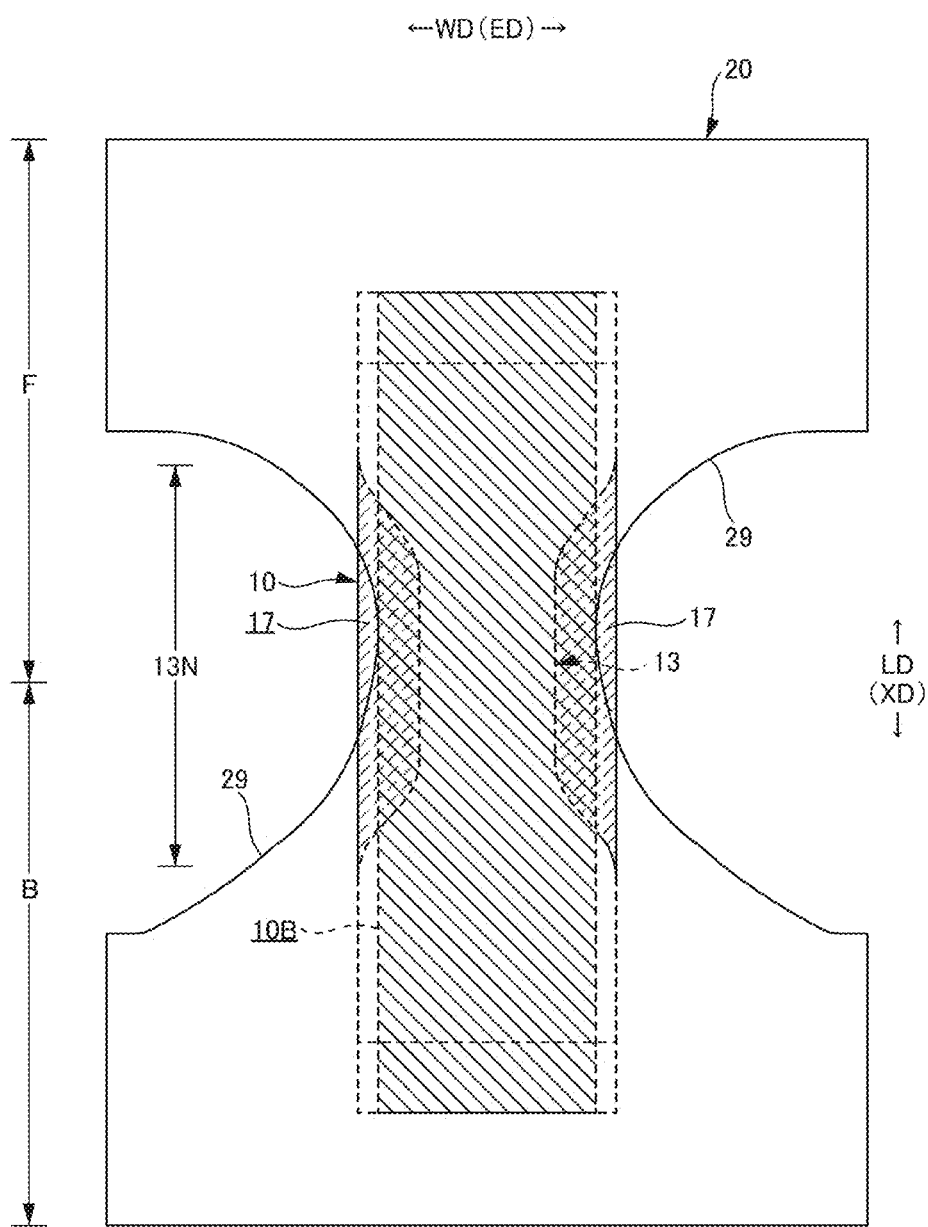

[FIG.4]
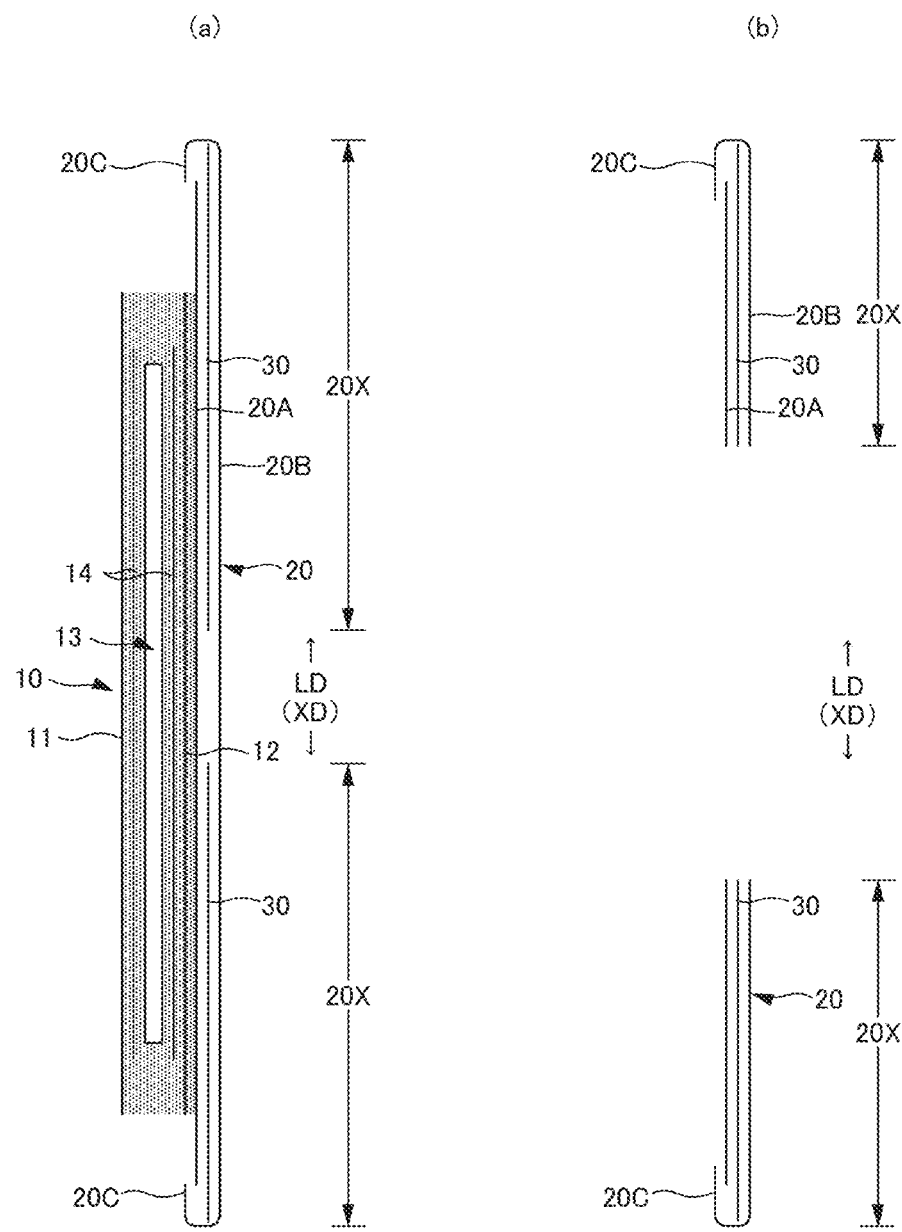

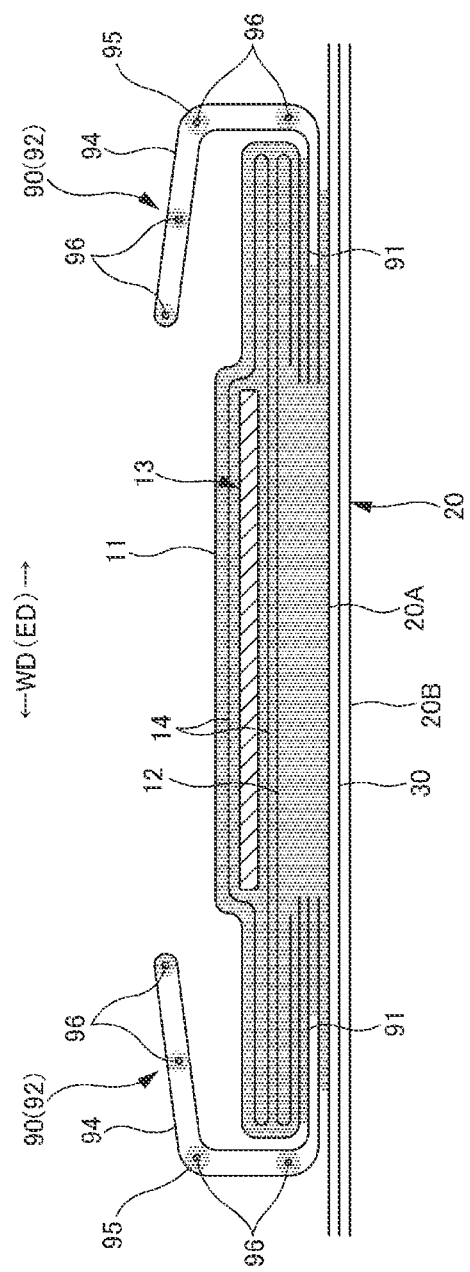

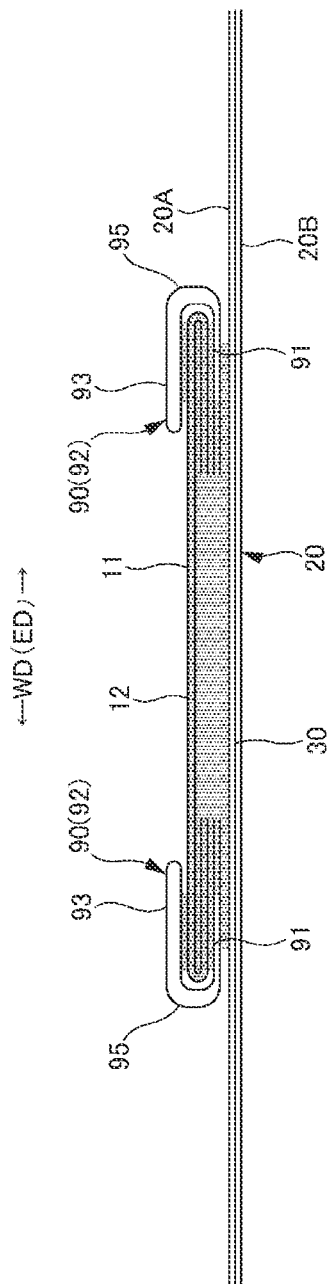

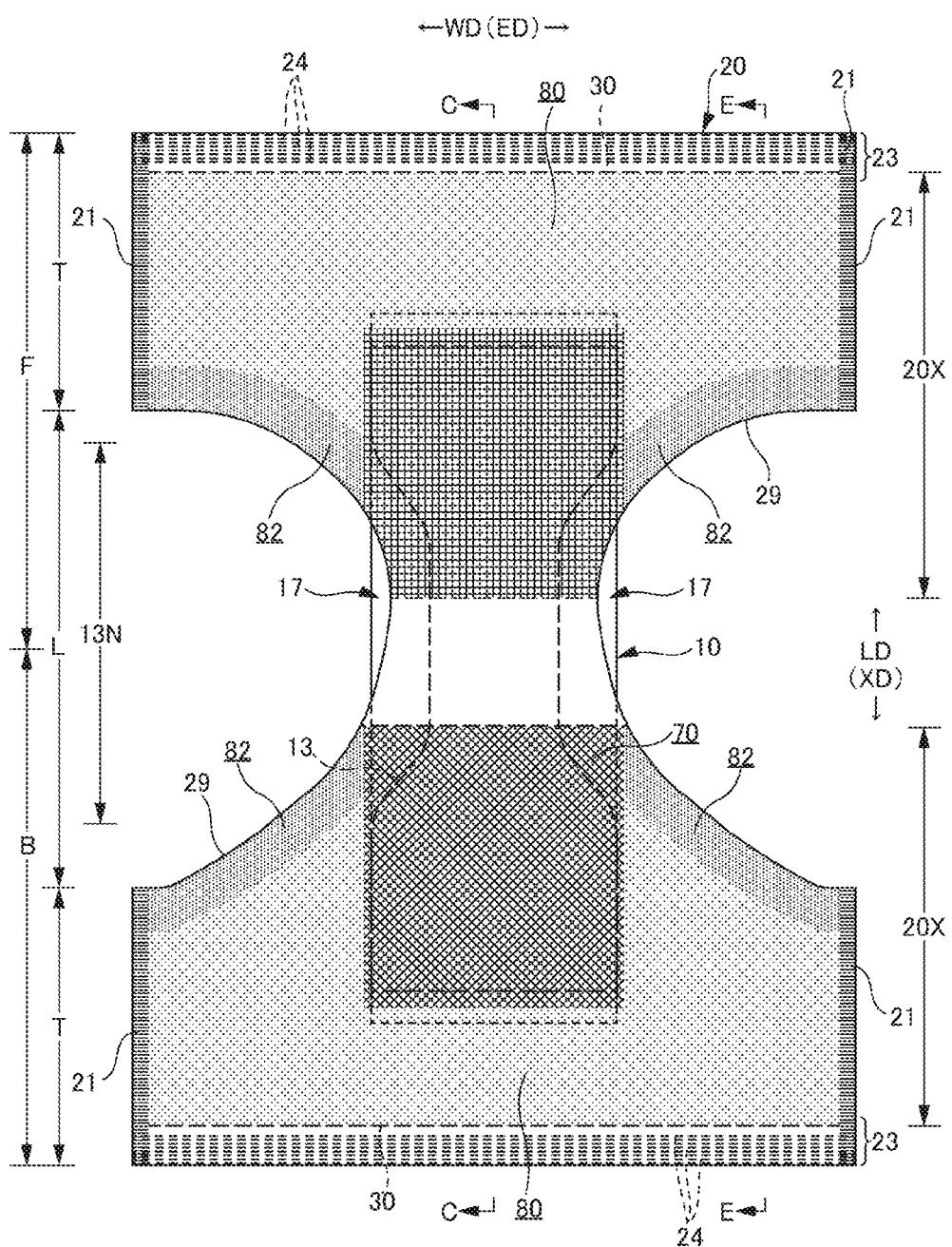
[FIG.7]

[FIG.8]
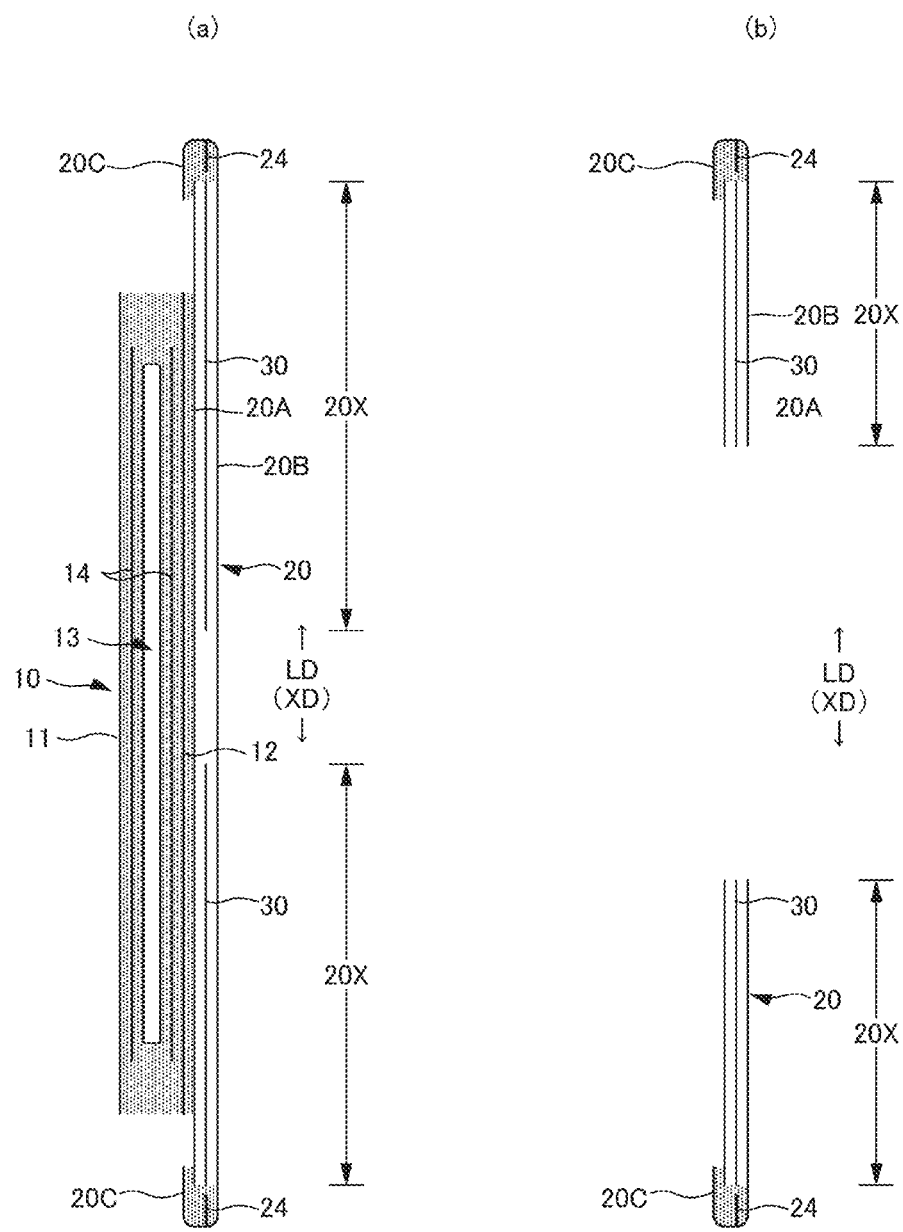

[FIG.9]
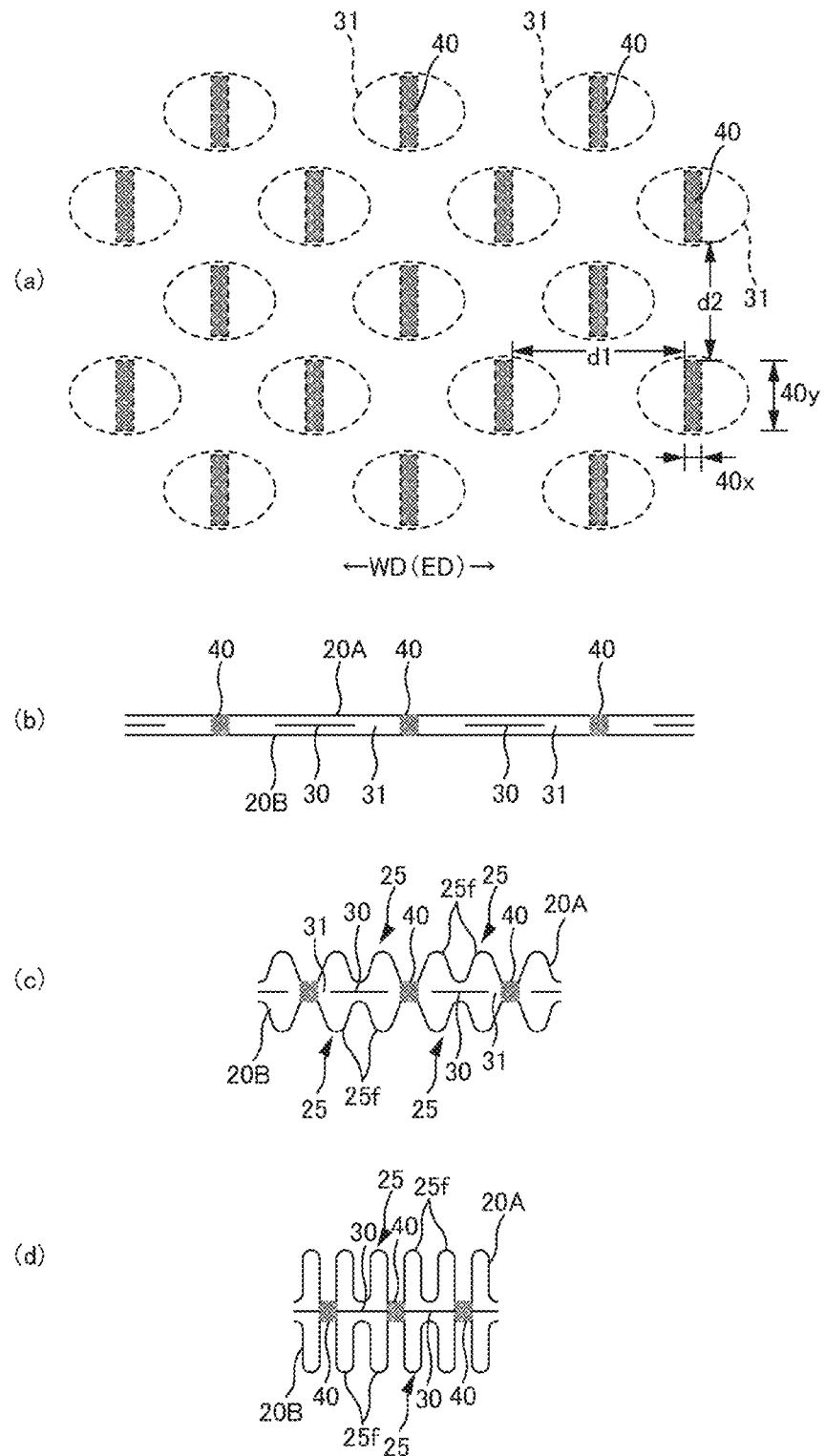

[FIG.10]
(a)
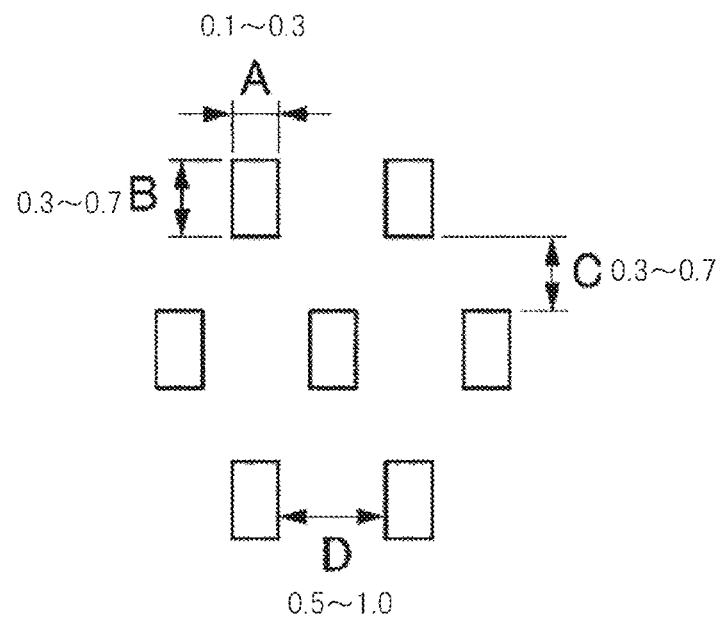
(b)
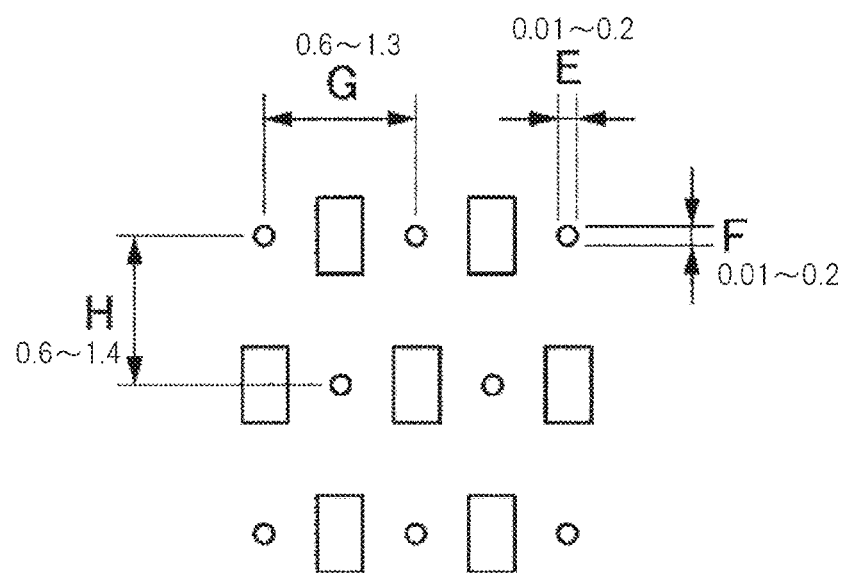

[FIG.11]
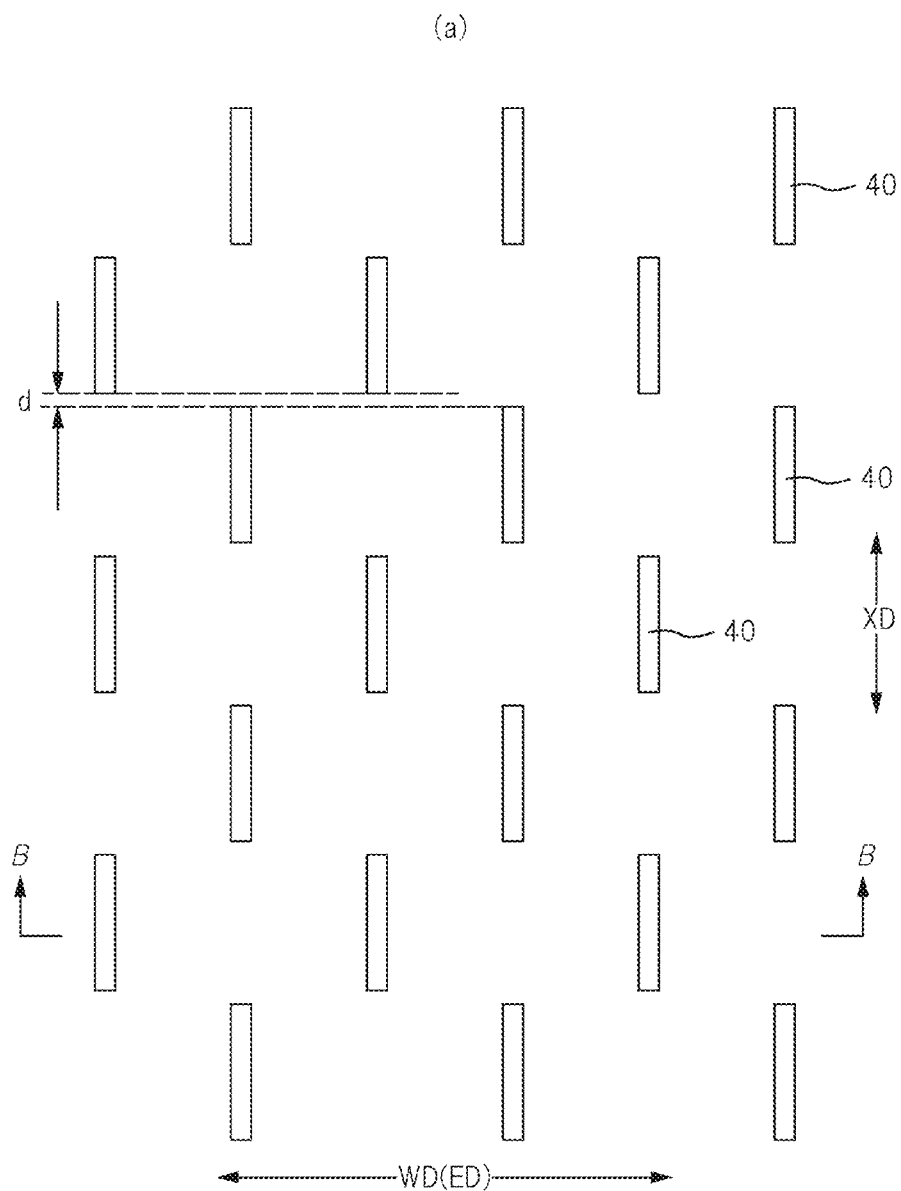
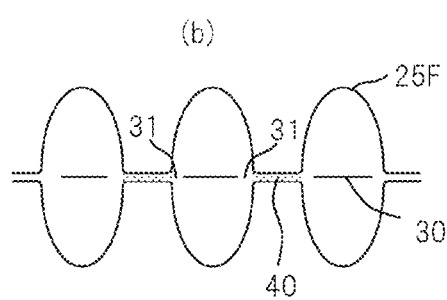

[FIG.12]
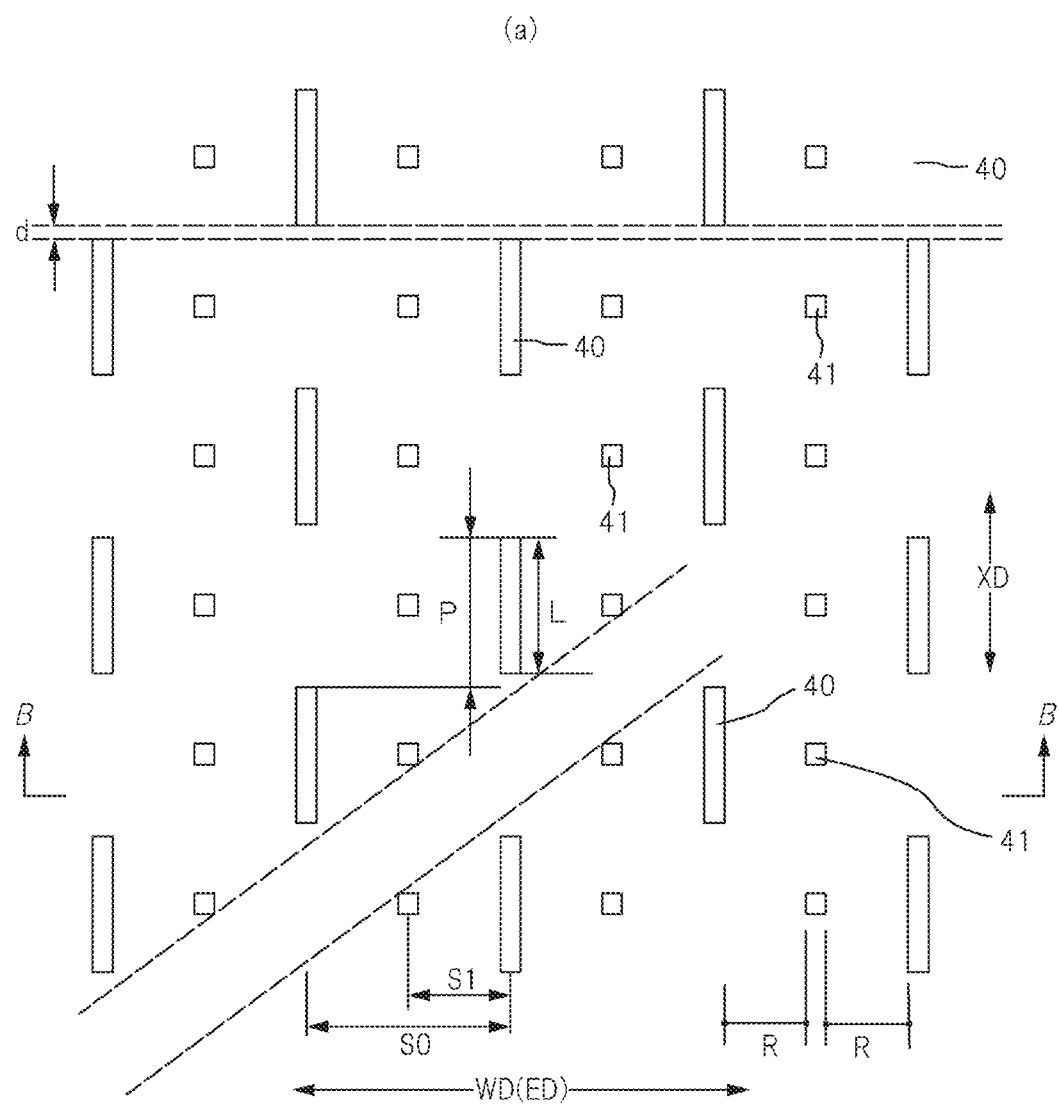

[FIG.13]
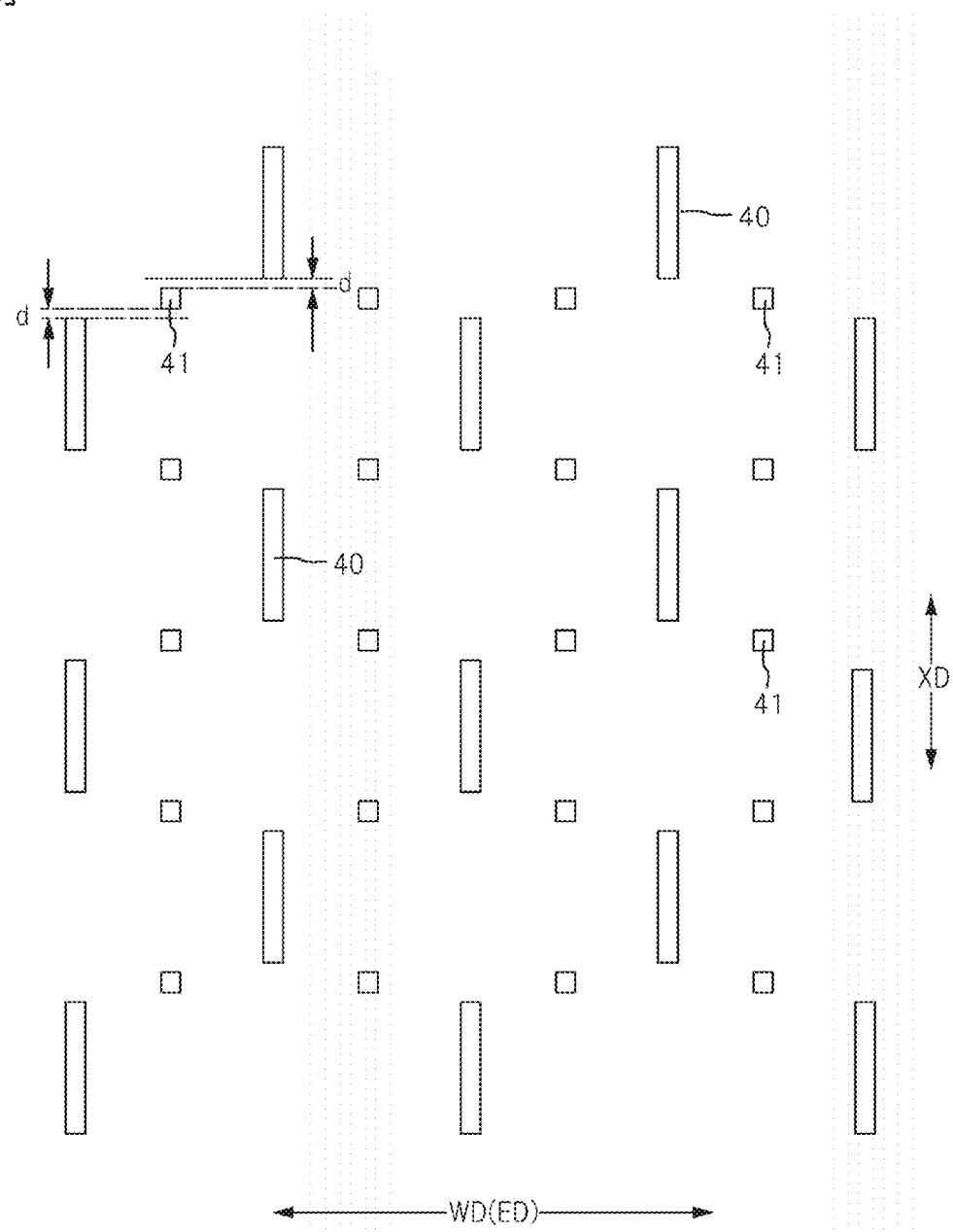

[FIG.14]
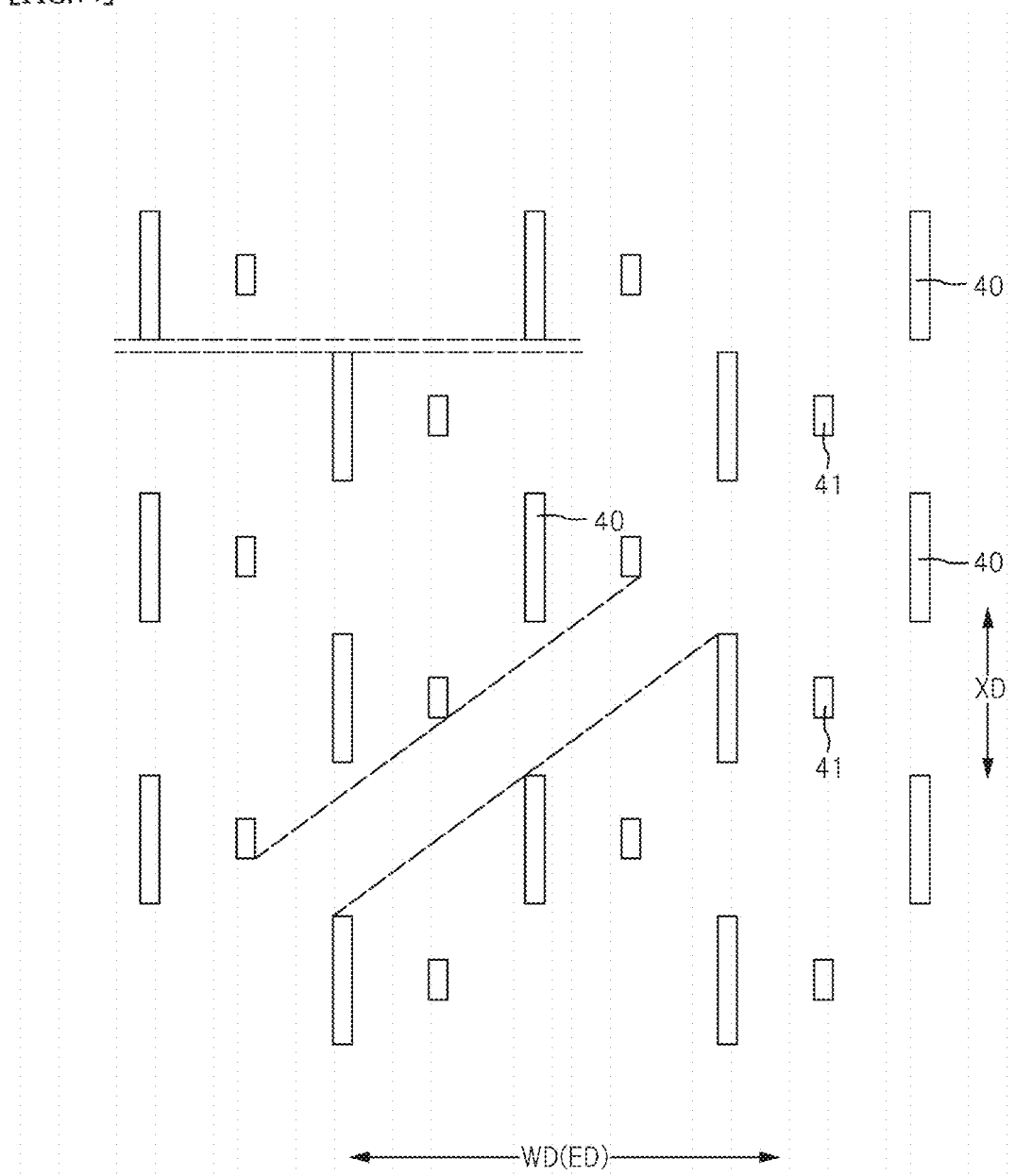

[FIG.15]
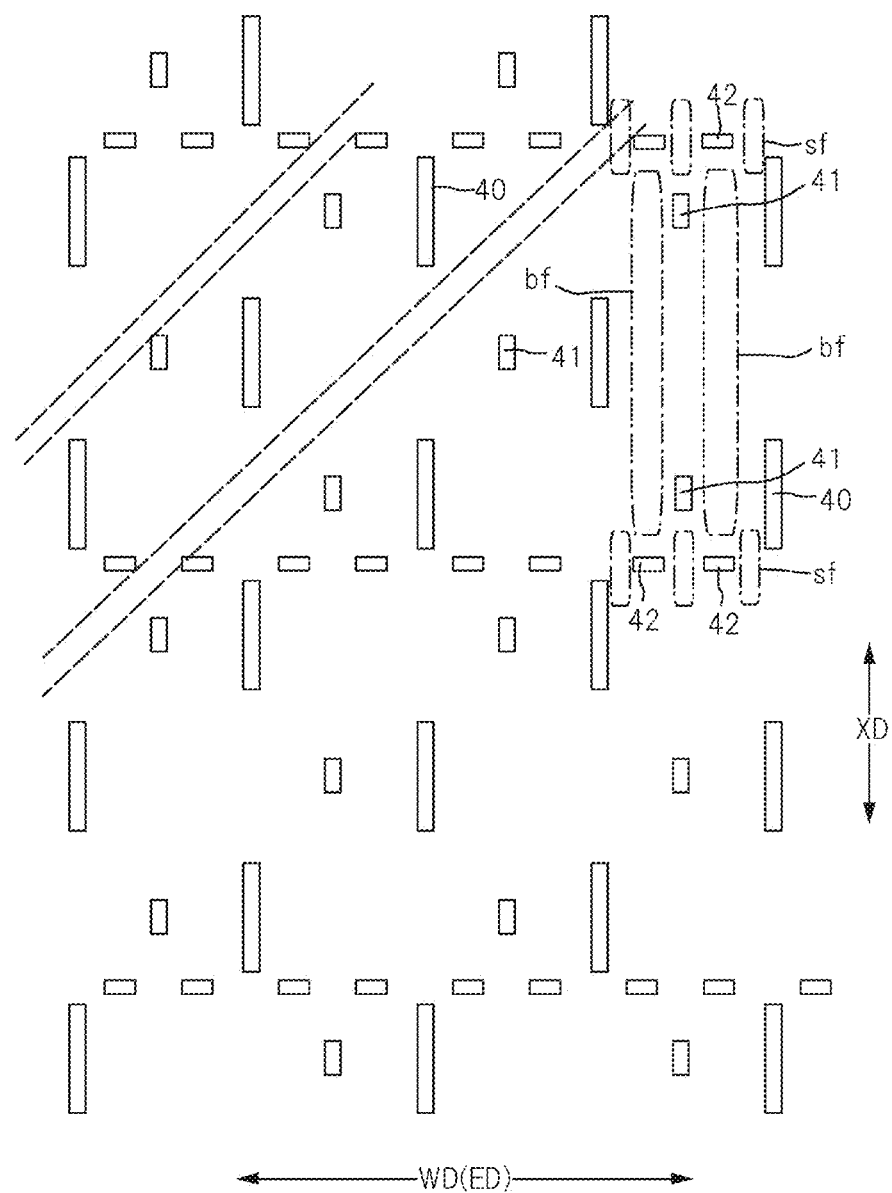

[FIG.16]
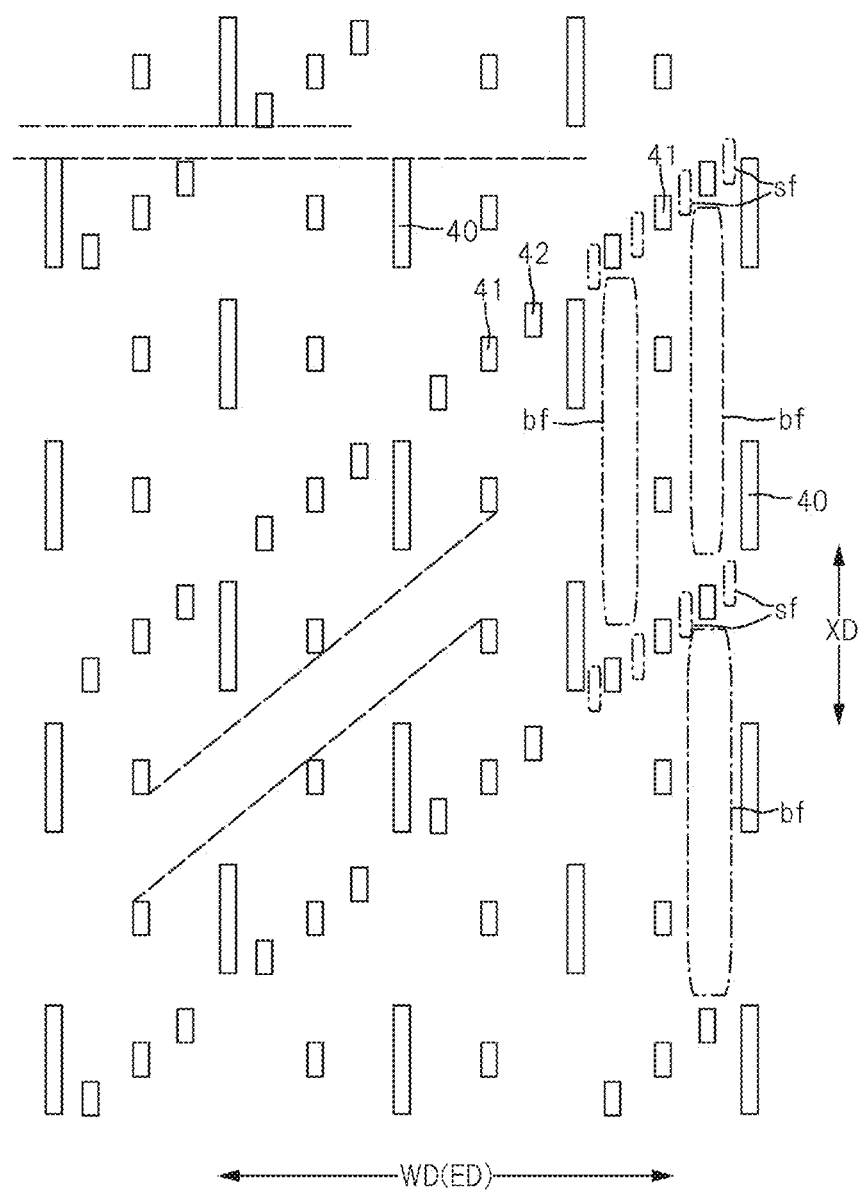

[FIG.17]
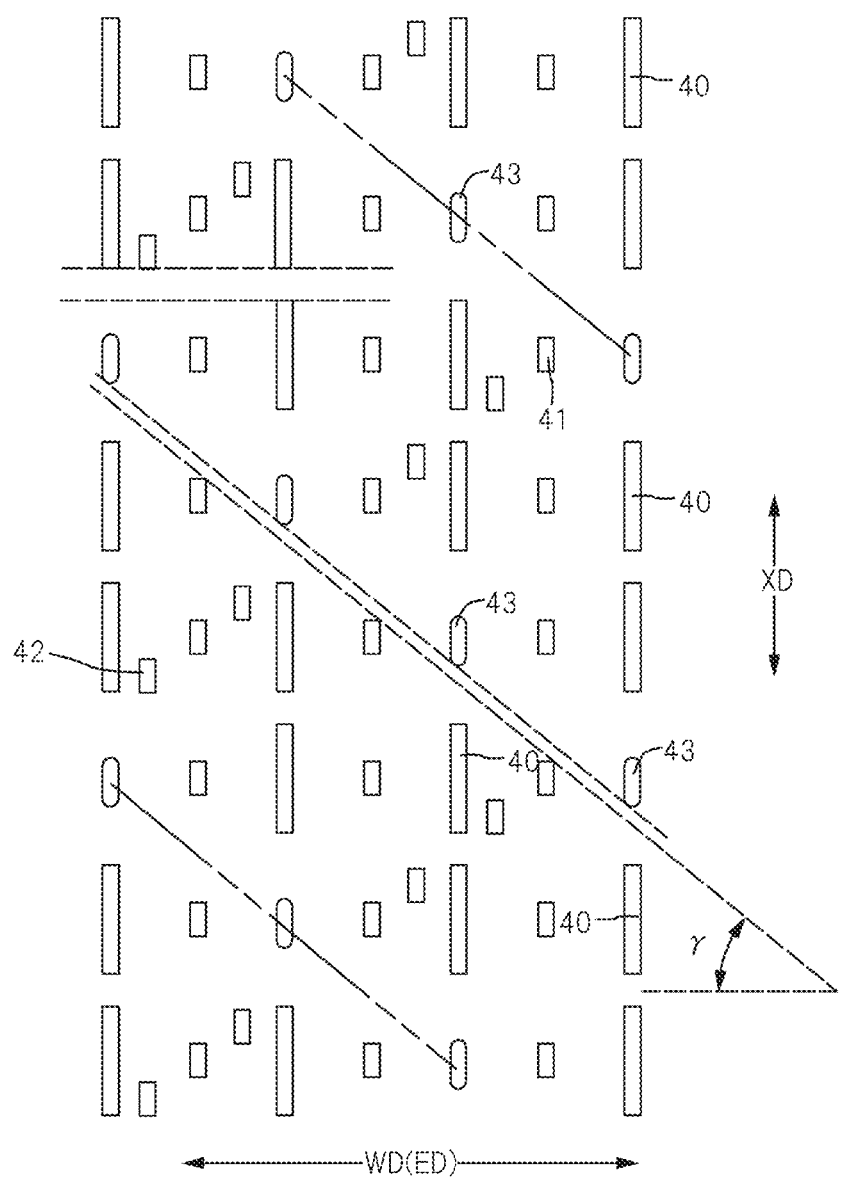

[FIG.18]
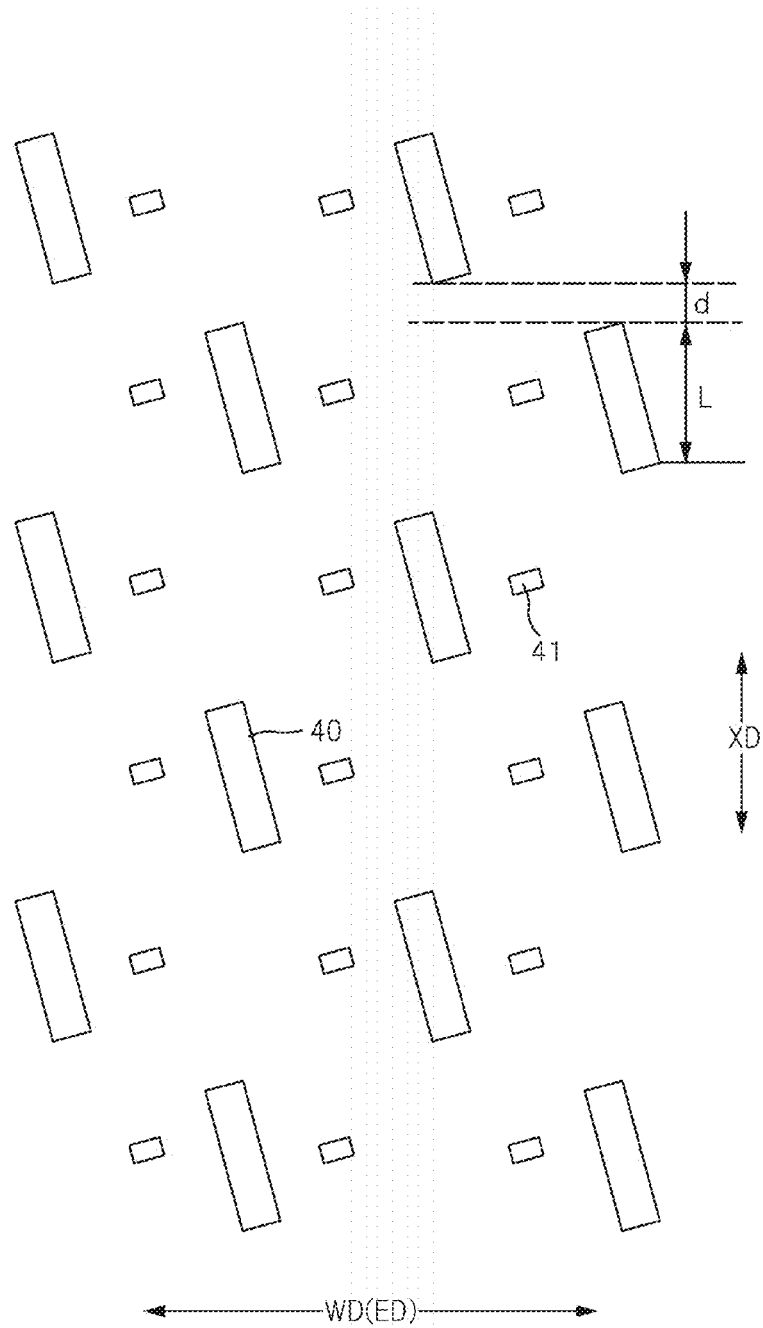

[FIG.19]
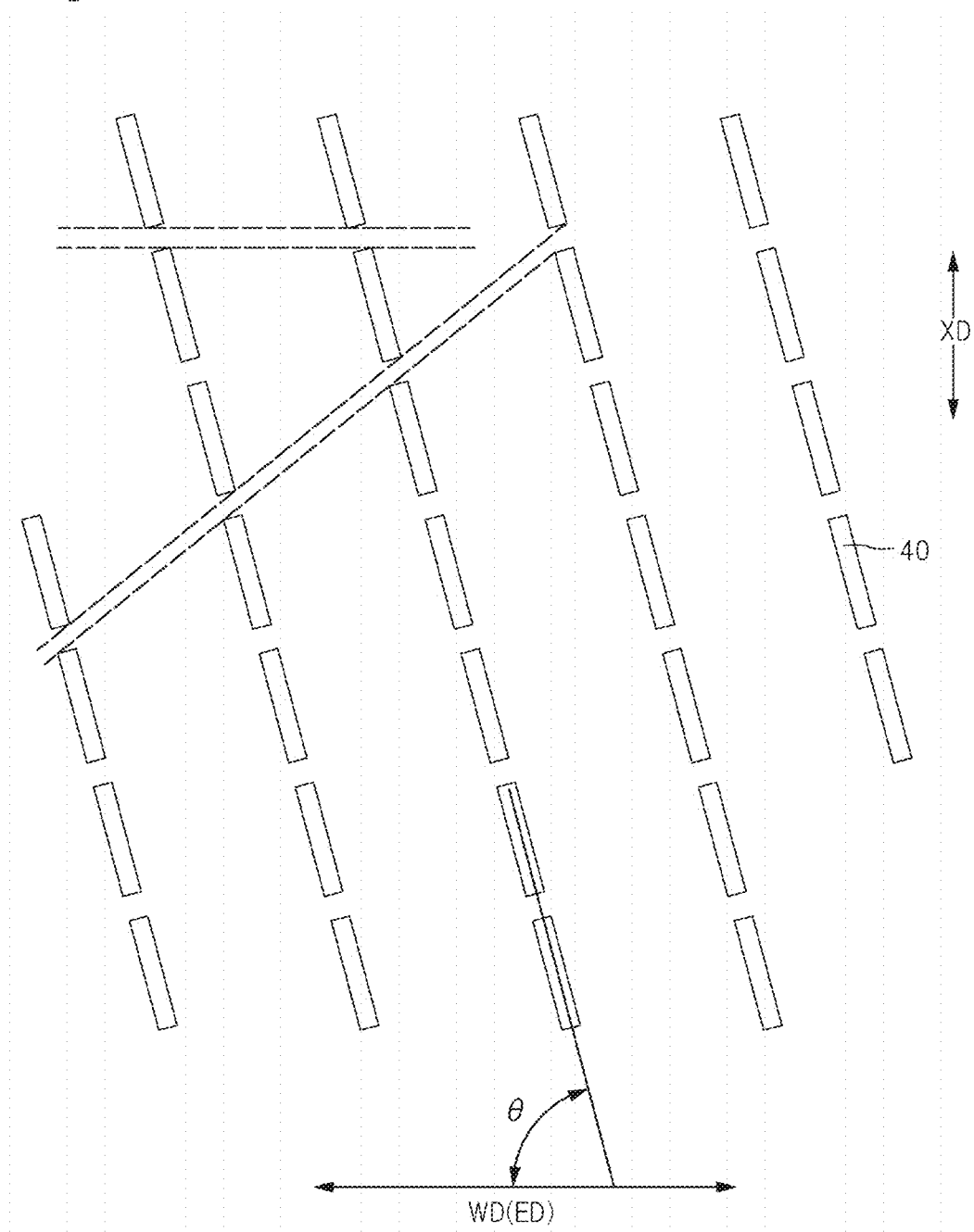

[FIG.20]
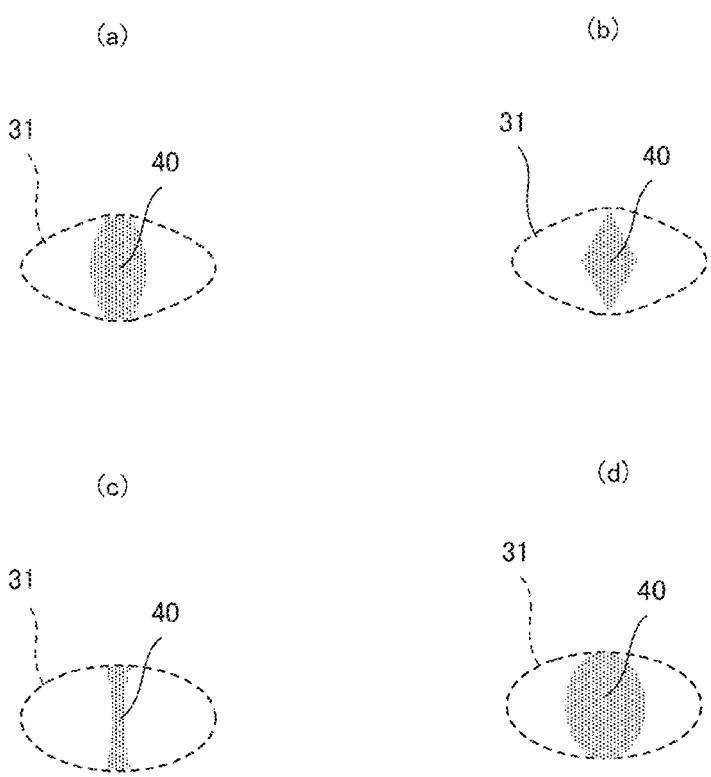

[FIG.21]
(a)
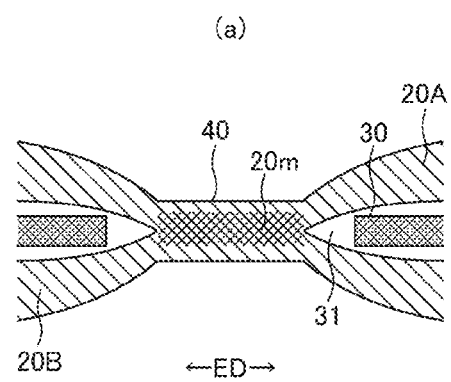
(b)
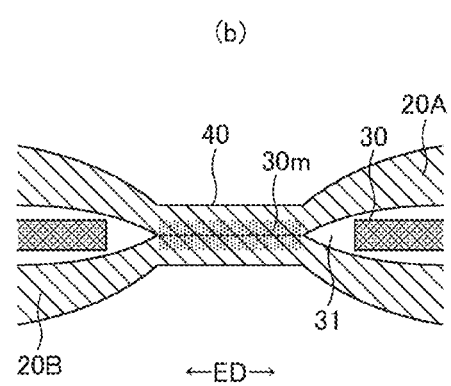
(c)
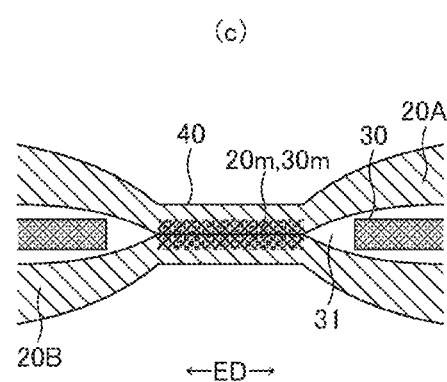

[FIG.22]
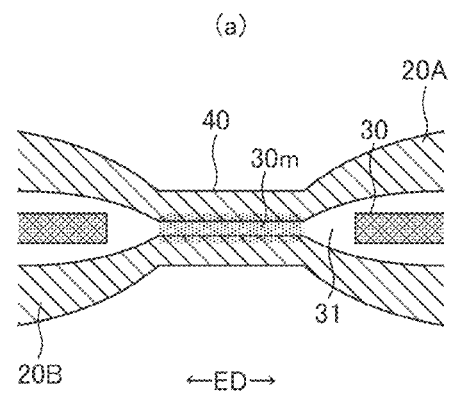
(a)
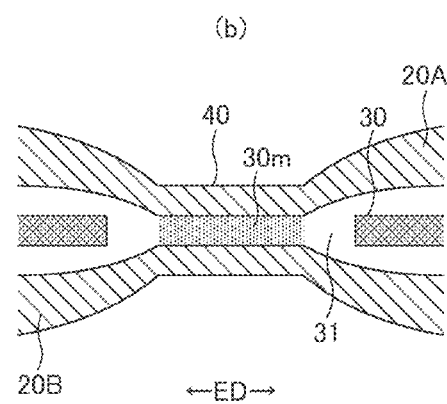
(b)
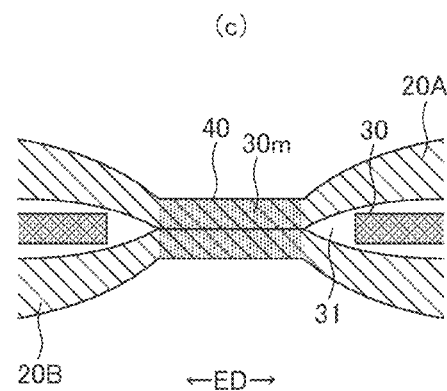
(c)

[FIG.23]
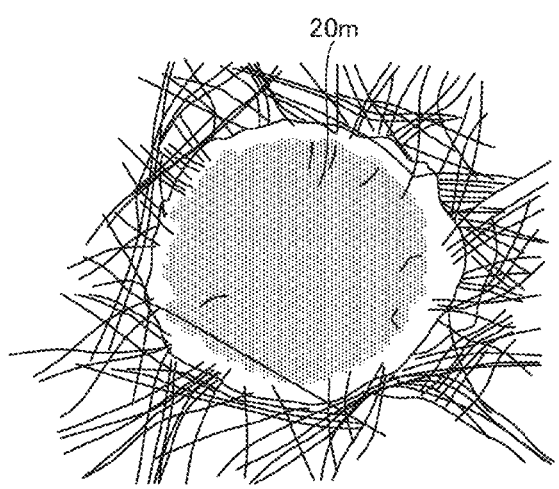
(b)
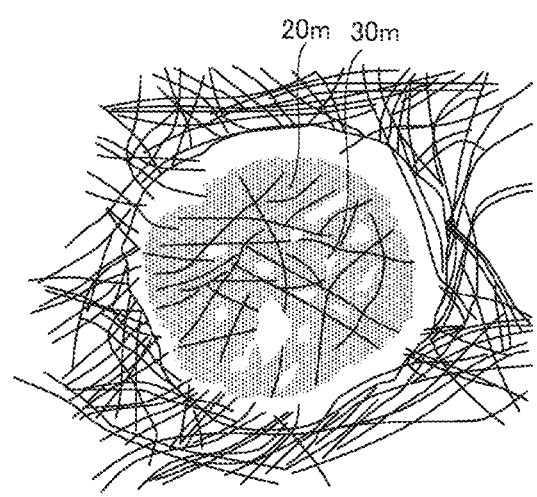

[FIG.24]
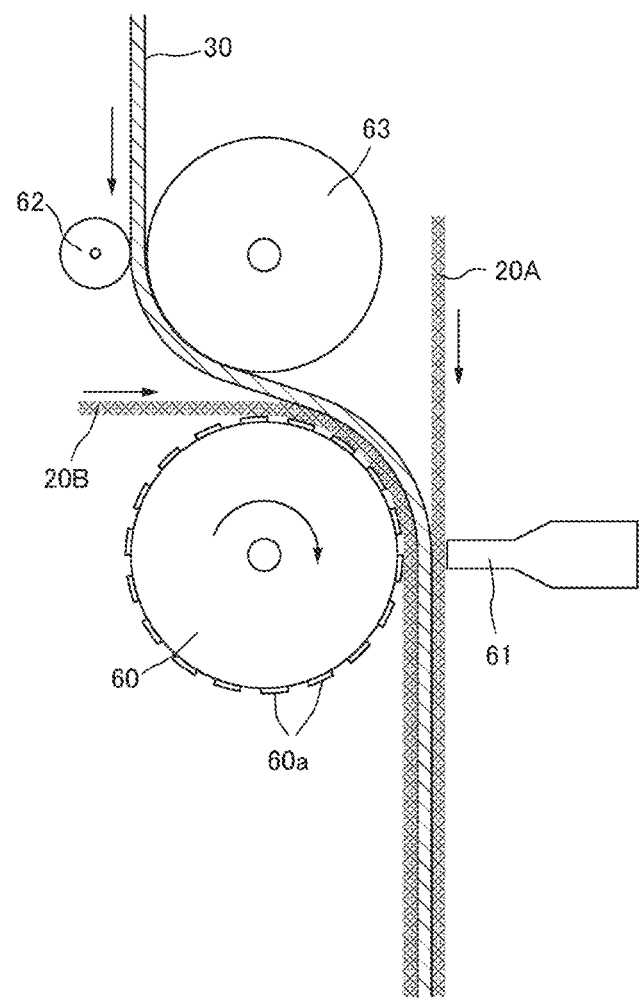

[FIG.25]
(a)
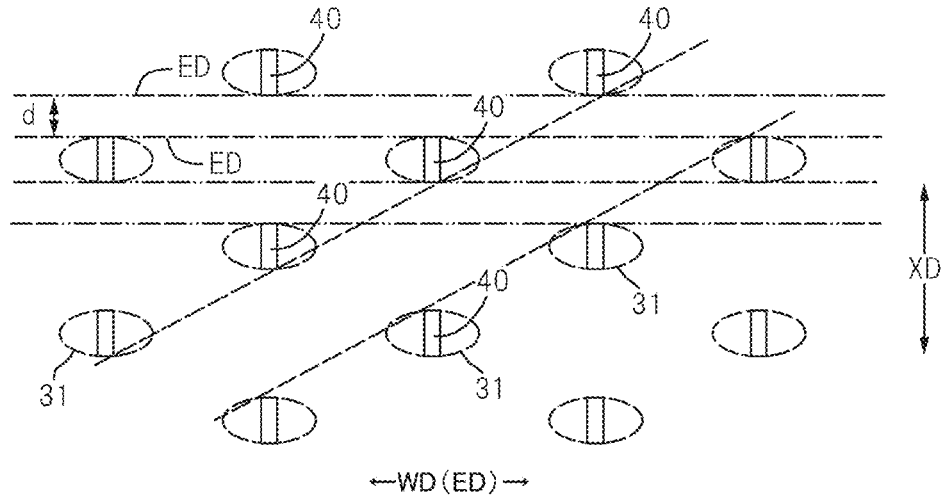
(b)
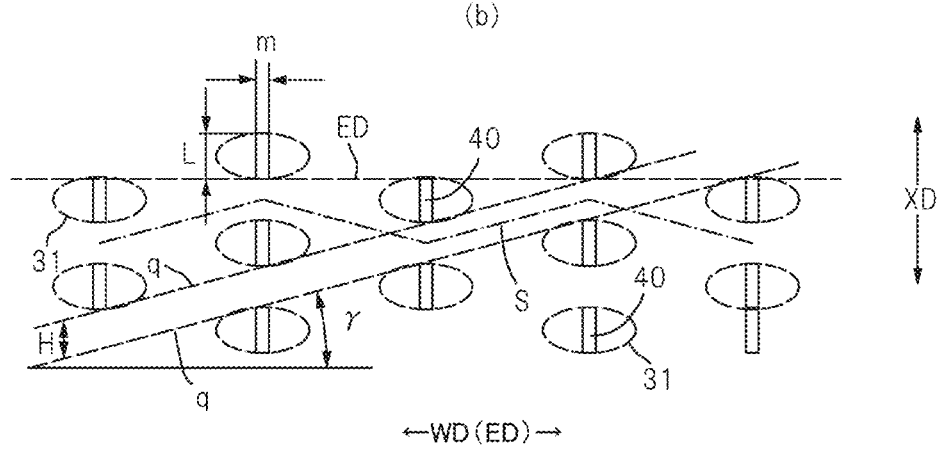
(c)
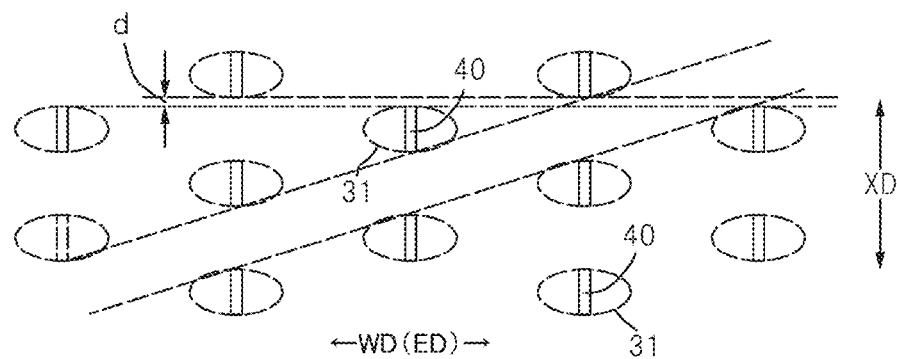

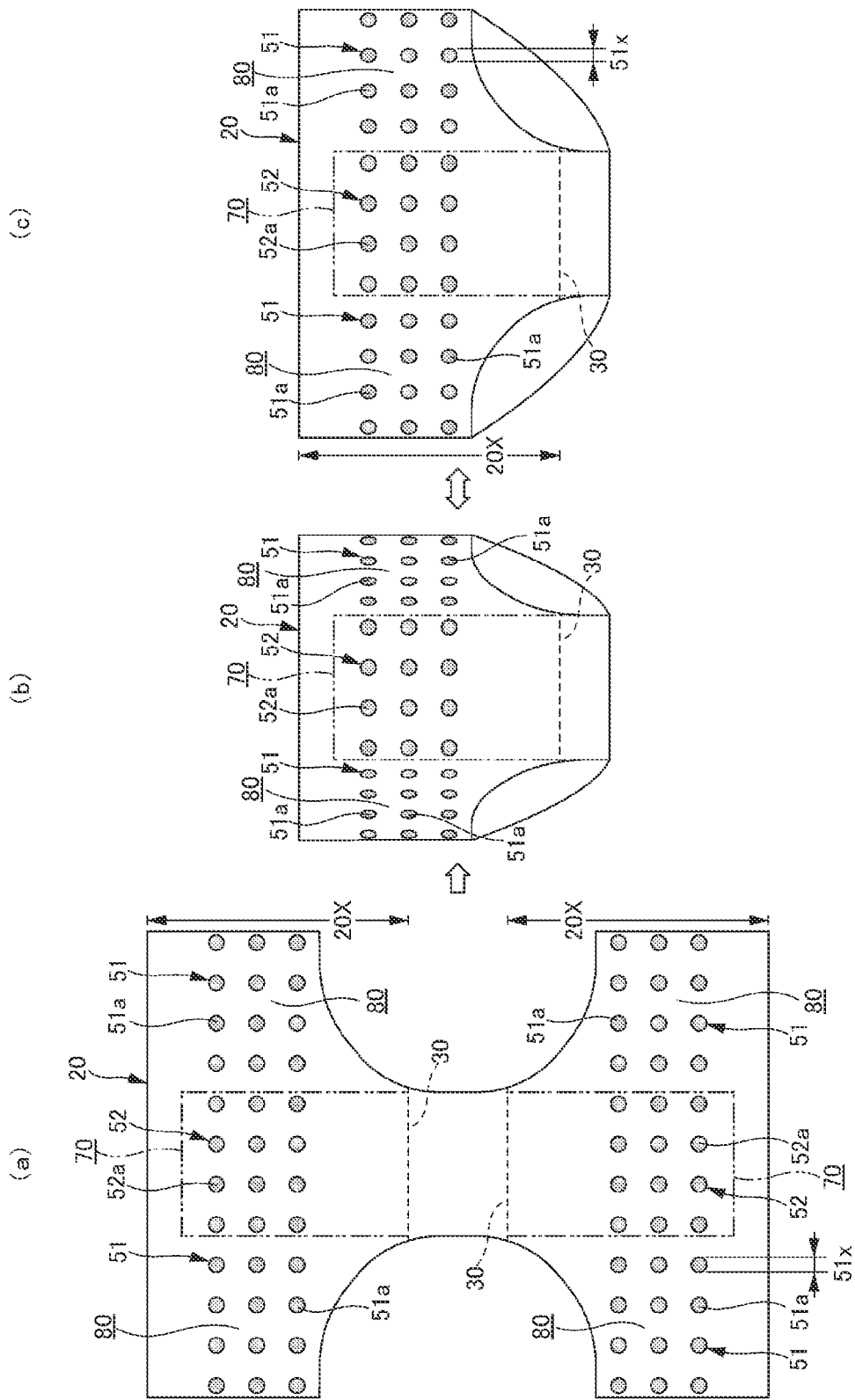
[FIG.26]

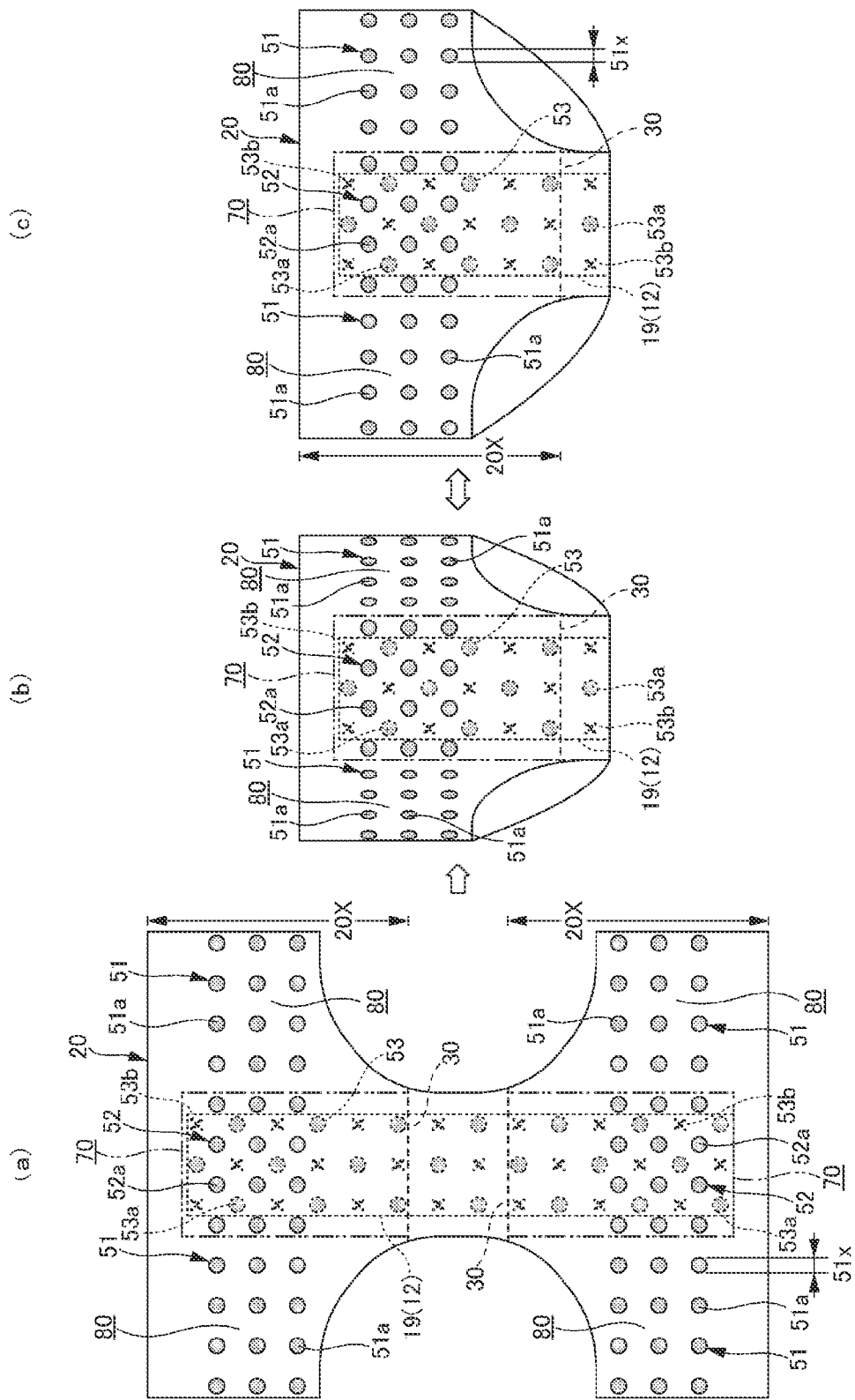
[FIG.27]

[FIG.28]
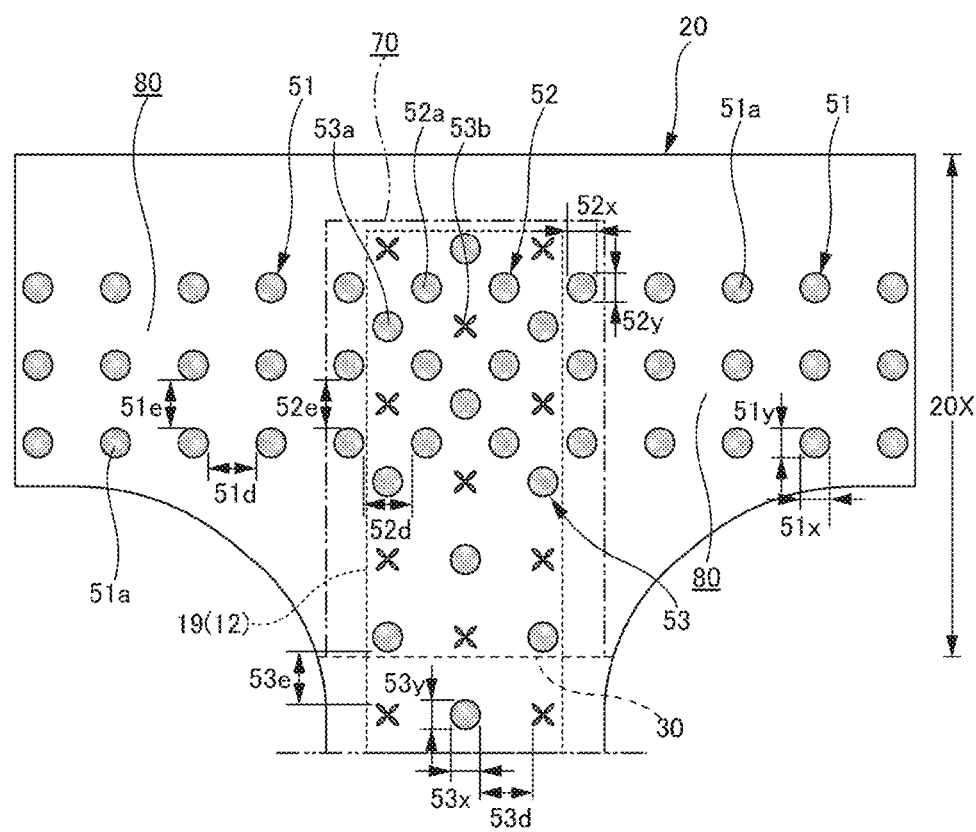

[FIG.29]
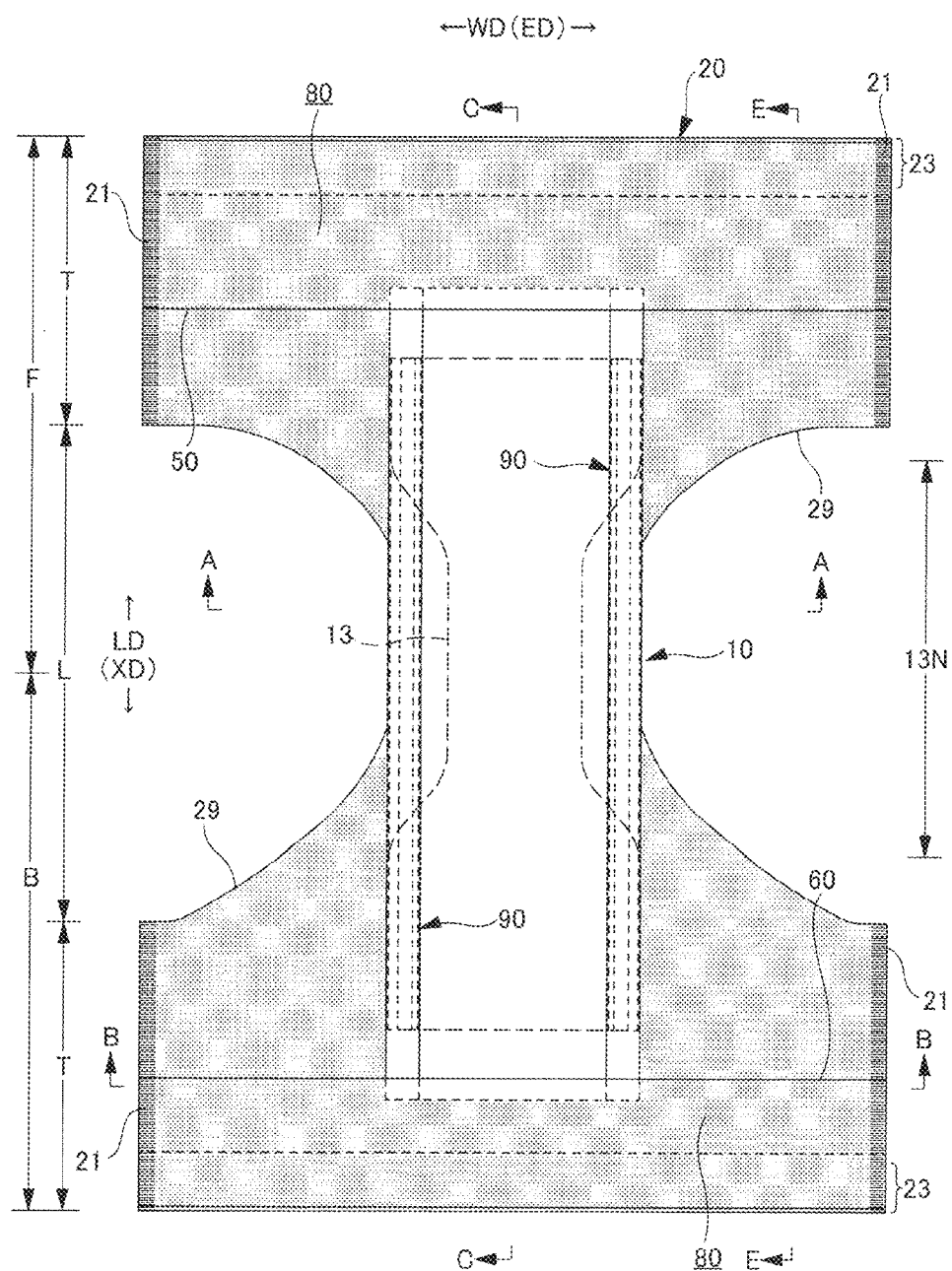

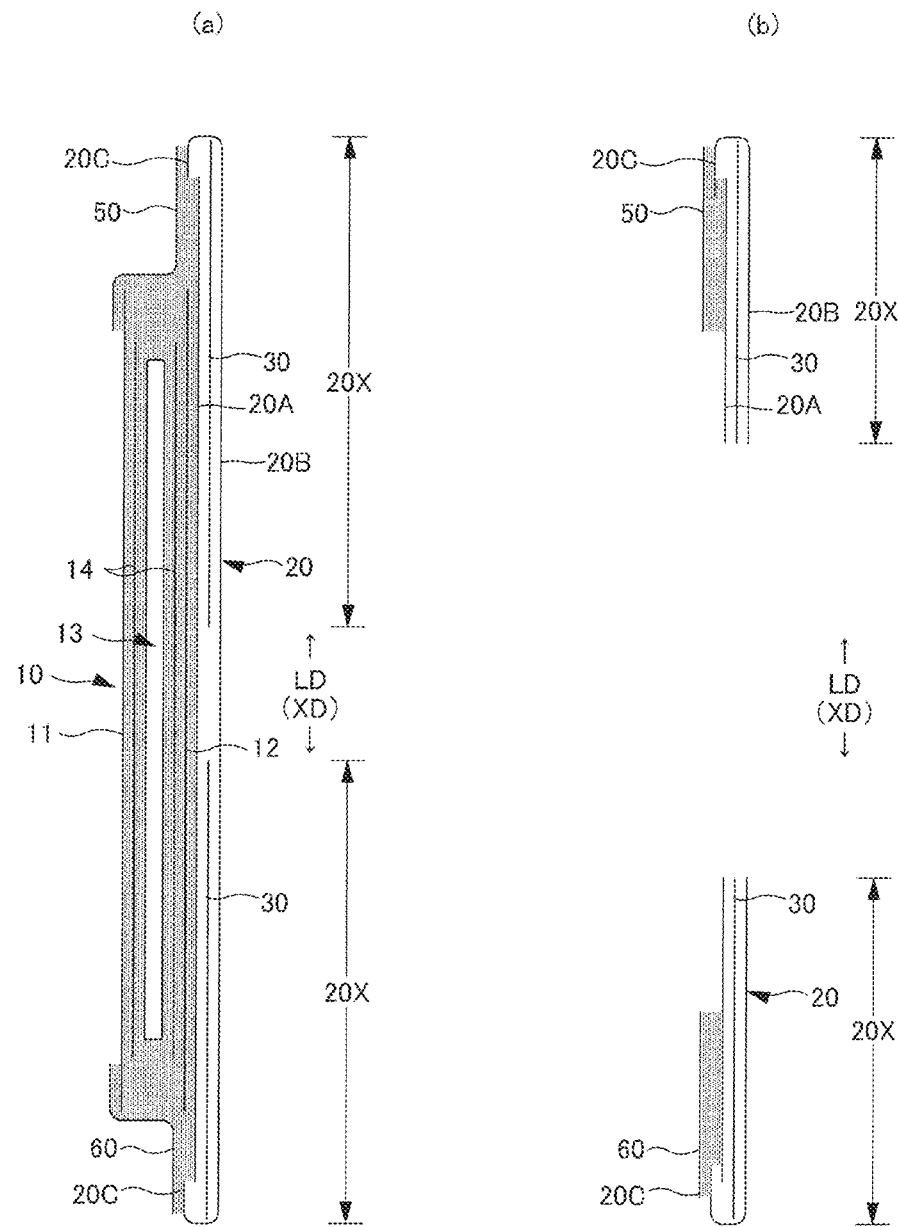
[FIG.30]

DISPOSABLE WEARABLE ARTICLE

CROSS-REFERENCE TO RELATED APPLICATIONS

This application is the U.S. national stage application of International Application PCT/JP2019/020582, filed May 24, 2019, which international application was published on Dec. 12, 2019, as International Publication WO 2019/235244 in the Japanese language. The International Application claims priority of Japanese Patent Application No. 2018-106829, filed Jun. 4, 2018. The international application and Japanese applications are both incorporated herein by reference, in entirety.

TECHNICAL FIELD

The present invention relates to a disposable wearable article including a stretchable region having a design printing section.

BACKGROUND ART

In a disposable wearable article such as a disposable diaper, it is common to impart elasticity to appropriate places such as around legs and around a waist in order to improve fitting to a body surface. As a method of imparting elasticity, conventionally, a method of attaching an elongated elastic member such as a rubber thread in a state of being stretched in a longitudinal direction thereof has been widely adopted. However, when it is desired to impart elasticity at a certain width, a mode is adopted in which rubber threads are fixed while being arranged side by side at intervals in the width. In addition, there has been a proposed method in which an elastic sheet is attached in a state of being stretched in an elasticity imparting direction as a material excellent in fitting as a surface. (For example, see Patent Literature 1).

A stretchable structure including this elastic sheet is obtained by stacking the elastic sheet between a first sheet layer and a second sheet layer, and bonding the first sheet layer and the second sheet layer through joint holes formed in the elastic sheet at a plurality of dot-shaped bonded portions arranged at intervals in a stretchable direction and a direction orthogonal thereto in a state in which the elastic sheet is stretched in the stretchable direction. The stretchable structure of the elastic sheet can be provided not only with a stretchable region in which elongation at elastic limit changes depending on the arrangement and area ratio of the bonded portions and the elongation at elastic limit changes, but also a non-stretchable region that hardly extends or contracts. In the stretchable region, in a natural length state, as the elastic sheet contracts between the bonded portions, an interval between the bonded portions becomes narrower, and pleats extending in a direction intersecting the stretchable direction are formed between the bonded portions in the first sheet layer and the second sheet layer. On the other hand, at the time of stretching, as the elastic sheet stretches between the bonded portions, the interval between the bonded portions and the pleats in the first sheet layer and the second sheet layer widen, and elastic stretching is allowed until a fully spread state of the first sheet layer and the second sheet layer.

The stretchable region by the elastic sheet is excellent in surface fitting is, is extremely flexible since there is no bonding between the first sheet layer and the second sheet layer, and the elastic sheet and bonding between the first sheet layer and the second sheet layer is extremely small, and has an advantage that the joint holes of the elastic sheet contribute to improvement of air permeability.

Meanwhile, a design is printed on the disposable wearable article, and examples of the design include a pattern for decoration (including picture and one-point character), function indication such as usage, use assistance, or size, or mark display such as a manufacturer, a product name, or a characteristic feature (for example, see 2). In general, such a design printing section is printed on a material such as a nonwoven fabric included in an outer surface of the disposable wearable article, or a printed sheet is attached.

In addition, when such a general method is applied to the stretchable region, there is a problem that the design greatly collapses due to formation of the pleats in the design print material in the natural length state. Thus, to solve this problem, it has been proposed to provide a stretchable region by a stretchable structure including an elastic sheet, and print a design on a part of the elastic sheet located in the stretchable region (for example, see Patent Literature 3). In this case, wrinkles or pleats are not formed by extension or contraction in the elastic sheet, and thus design collapse due to formation of the wrinkles or pleats on a prink target of the design does not occur. Furthermore, when the entire design uniformly extends or contracts, a shape of the design is uniformly deformed, and thus the overall balance of the design is not lost.

However, in the case of providing the non-stretchable region to the stretchable structure including the elastic sheet, when a uniform print is applied to a part corresponding to the stretchable region and a part corresponding to the non-stretchable region in the elastic sheet, the elastic sheet hardly contracts in the non-stretchable region, whereas the elastic sheet contracts to some extent in the stretchable region during wearing. Thus, a difference in design appearance becomes large between the stretchable region and the non-stretchable region. In particular, in the case of not being equal between the two regions, there is a problem that distortion of one of the regions is noticeable.

In order to improve the appearance of the design of the stretchable region in a worn state, it may be considered that the design is not printed only on the part of the elastic sheet located in the non-stretchable region. However, since it is generally difficult to stably position a non-printed part in the non-stretchable region during manufacturing, it is desired to uniformly print the design on the elastic sheet.

CITATION LIST

Patent Literature

Patent Literature 1: JP 5967736 B1
Patent Literature 2: JP 2015-204982 A

SUMMARY OF INVENTION

Technical Problem

Therefore, a main object of the invention is to reduce the difference in design appearance between the stretchable region and the non-stretchable region in the worn state.

Solution to Problem

Disposable wearable articles solving the above problems are as follows.

<First Aspect>

A disposable wearable article having an elastic sheet stretchable structure in which an elastic sheet is stacked between a first sheet layer and a second sheet layer, and the first sheet layer and the second sheet layer are bonded through joint holes penetrating the elastic sheet or with the elastic sheet interposed therebetween at a plurality of bonded portions arranged at intervals, in which a region having the elastic sheet stretchable structure has a stretchable region which contracts in a stretchable direction by a contraction force of the elastic sheet and is stretchable in the stretchable direction, and a non-stretchable region, a part of the elastic sheet located in the stretchable region is printed with a first design including design elements, a part of the elastic sheet located in the non-stretchable region is printed with a second design including design elements, the first design and the second design are the same when the stretchable region and the non-stretchable region are at an elongation at elastic limit, and a stretchable direction dimension of the design elements of the first design when a stretch rate of the stretchable region is 130% or more is 80% or more of a stretchable direction dimension of the design elements of the first design when the stretchable region is at the elongation at elastic limit.

(Function and Effect)

In this disposable wearable article, the first design and the second design are the same when the stretchable region and the non-stretchable region are at the elongation at elastic limit. This description merely means that uniform printing is applied to the part corresponding to the stretchable region and the part corresponding to the non-stretchable region in the elastic sheet. In addition, in this disposable wearable article, the stretchable direction dimension of the design elements of the first design when the stretch rate of the stretchable region is 130% or more, that is, in a general worn state is 80% or more the stretchable direction dimension of the design elements of the first design when the stretchable region is at the elongation at elastic limit. For this reason, there is little difference in appearance between the designs in the stretchable region and the non-stretchable region during wearing.

Note that "the same" with respect to the first design and the second design means that the design elements have the same dimensions, shapes, orientations, arrangements, etc. However, it is natural that the areas of the designs, the number of design elements that change depending on the area, or discontinuity, missing, etc. of the design elements may be different. In addition, "design elements" are elements included in a distinguishable part as a part different from other parts in the design, and is not particularly limited.

<Second Aspect>

The disposable wearable article according to the first aspect, including:

a region having the elastic sheet stretchable structure and a region not having the elastic sheet stretchable structure which is continuous with the region having the elastic sheet stretchable structure, and a non-stretchable sheet other than the elastic sheet extending from the non-stretchable region to the region not having the elastic sheet stretchable structure, in which the non-stretchable sheet is printed with a third design including a design element, and the third design includes design elements which are the same as the design elements of the first design when the stretchable region and the non-stretchable region are at the elongation at elastic limit.

(Function and Effect)

In general, the disposable wearable article does not frequently have a stretchable structure as a whole. This description is similarly applied to the case of adopting the elastic sheet stretchable structure. Therefore, in the disposable wearable article having the elastic sheet stretchable structure, to add a design to a wider range, as in this aspect, it is preferable to provide the third design to a non-stretchable sheet other than the elastic sheet extending from the non-stretchable region to a region not having the elastic sheet stretchable structure. In this case, similarly to a relationship between the first design and the second design, to enhance integrity of the design, the third design preferably includes design elements which are the same as the design elements of the first design when the stretchable region and the non-stretchable region are at the elongation at elastic limit. In this way, the difference in appearance between the first design and the third design decreases in the worn state.

Note that "the same" design elements with respect to the first design and the third design means that dimensions and shapes are the same, and colors and directions may be different.

In addition, a technical feature of the second aspect may not require the second design. Therefore, it is significant even when the second design is not provided. That is, the following disposable wearable article is possible.

<Application Example of Second Aspect>

A disposable wearable article having an elastic sheet stretchable structure in which an elastic sheet is stacked between a first sheet layer and a second sheet layer, and the first sheet layer and the second sheet layer are bonded through joint holes penetrating the elastic sheet or with the elastic sheet interposed therebetween at a plurality of bonded portions arranged at intervals, in which a region having the elastic sheet stretchable structure contracts in a stretchable direction by a contraction force of the elastic sheet, and has a stretchable region which is stretchable in the stretchable direction and a non-stretchable region, a region having the elastic sheet stretchable structure and a region not having the elastic sheet stretchable structure which is continuous with the region having the elastic sheet stretchable structure are included, a non-stretchable sheet other than the elastic sheet extending from the non-stretchable region to the region not having the elastic sheet stretchable structure is included, a part of the elastic sheet located in the stretchable region is printed with a first design including design elements, the non-stretchable sheet is printed with a third design including design elements, the third design includes design elements which are the same as the design elements of the first design when the stretchable region and the non-stretchable region are at an elongation at elastic limit, and a stretchable direction dimension of the design elements of the first design when a stretch rate of the stretchable region is 130% or more is 80% or more of a stretchable direction dimension of the design elements of the first design when the stretchable region is at the elongation at elastic limit.

\<Third Aspect\>

The disposable wearable article according to the second aspect, in which design elements are arranged at intervals in at least one of the second design and the third design, at least parts of the second design and the third design overlap each other, a minimum value of a stretchable direction interval of design elements arranged in the stretchable direction in one of the second design and the third design is larger than a minimum value of a stretchable direction dimension of design elements in the other design, and a minimum value of an orthogonal direction interval of design elements arranged in an orthogonal direction orthogonal to the stretchable direction in the one design is larger than a minimum value of an orthogonal direction dimension of design elements in the other design.

(Function and Effect)

In the case of providing the second design and the third design described above, in the non-stretchable region, there is concern that the design elements of the second design of the elastic sheet and the design elements of the third design of the non-stretchable sheet may overlap with each other, resulting in a cluttered appearance. Therefore, it is preferable that an interval of design elements of one design is sufficiently sparse with respect to a size of design elements of the other design, the design elements rarely overlap each other when compared to the other case, and clutter in appearance is suppressed as in this aspect.

In addition, a technical feature of the third aspect has significance in a case other than a case where "the third design includes design elements which are the same as the design elements of the first design when the stretch rate of the stretchable region is 130 to 170%". That is, the following disposable wearable article is preferable.

\<Application Example of Third Aspect\>

A disposable wearable article having an elastic sheet stretchable structure in which an elastic sheet is stacked between a first sheet layer and a second sheet layer, and the first sheet layer and the second sheet layer are bonded through joint holes penetrating the elastic sheet or with the elastic sheet interposed therebetween at a plurality of bonded portions arranged at intervals, in which a region having the elastic sheet stretchable structure has a stretchable region which contracts in a stretchable direction by a contraction force of the elastic sheet and is stretchable in the stretchable direction, and a non-stretchable region, a region having the elastic sheet stretchable structure and a region not having the elastic sheet stretchable structure which is continuous with the region having the elastic sheet stretchable structure are included, a non-stretchable sheet other than the elastic sheet extending from the non-stretchable region to the region not having the elastic sheet stretchable structure is included, a part of the elastic sheet located in the non-stretchable region is printed with a second design including design elements, the non-stretchable sheet is printed with a third design including design elements, the third design is a design in which design elements are arranged at intervals, at least parts of the second design and the third design overlap each other, a minimum value of a stretchable direction interval of design elements arranged in the stretchable direction in one of the second design and the third design is larger than a minimum value of a stretchable direction dimension of design elements in the other design, and a minimum value of an orthogonal direction interval of design elements arranged in an orthogonal direction orthogonal to the stretchable direction in the one design is larger than a minimum value of an orthogonal direction dimension of design elements in the other design.

\<Fourth Aspect\>

The disposable wearable article according to any one of the first to third aspects, in which the disposable wearable article is an underpants-type disposable wearable article including an integral outer body covering a front body and a back body or an outer body separately provided to the front body and the back body, an inner body attached to an intermediate portion of the outer body in a width direction and extending to both front and back sides of a crotch portion, side seal portions obtained by bonding both side portions of the outer body in the front body and both side portions of the outer body in the back body, respectively, a waist opening, a pair of right and left leg openings, and an absorber included in the inner body and extending to the both front and back sides of the crotch portion, wherein the outer body in at least one of the front body and the back body has an absorber region defined as a front-back direction range overlapping the absorber, and the elastic sheet stretchable structure is provided over at least a width direction range corresponding to a part between the side seal portions in the absorber region so that a stretchable direction thereof becomes the width direction, and in the absorber region, an intermediate portion in the width direction is the non-stretchable region, and a width direction range corresponding to a part between the non-stretchable region and the side seal portions is the stretchable region.

(Function and Effect)

In the case of providing the stretchable region in the outer body of the underpants-type disposable wearable article, it is desirable to arrange the elastic sheet in a part of the outer body overlapping the absorber for manufacturing reasons. However, the part is a region not requiring extension and contraction, and is generally set to the non-stretchable region. Therefore, the above-mentioned first design and second design are particularly preferable for such an underpants-type disposable wearable article.

Advantageous Effects of Invention

According to the invention, it is possible to reduce the difference in design appearance between the stretchable region and the non-stretchable region in the worn state.

BRIEF DESCRIPTION OF DRAWINGS

FIG. 1 is a plan view (internal surface side) of an underpants-type disposable diaper in a spread state.

FIG. 2 is a plan view (external surface side) of the underpants-type disposable diaper in the spread state.

FIG. 3 is a plan view illustrating only a main part of the underpants-type disposable diaper in the spread state.

FIG. 4(a) is a cross-sectional view taken along line C-C of FIG. 1, and FIG. 4(b) is a cross-sectional view taken along line E-E of FIG. 1.

FIG. 5 is a cross-sectional view taken along line A-A of FIG. 1.

FIG. 6 is a cross-sectional view taken along line B-B of FIG. 1.

FIG. 7 is a plan view (internal surface side) of a main part of a stretchable region in the underpants-type disposable diaper in the spread state.

FIG. 8(a) is a cross-sectional view corresponding to line C-C of FIG. 1, and FIG. 8(b) is a cross-sectional view corresponding to line E-E of FIG. 1.

FIG. 9 is a plan view and a cross-sectional view illustrating an arrangement example of bonded portions.

FIG. 10 is a plan view illustrating an arrangement example of the bonded portions.

FIG. 11 illustrates an arrangement example of the bonded portions, in which FIG. 11(a) is a plan view, and FIG. 11(b) is a cross-sectional view taken along line B-B.

FIG. 12 illustrates an arrangement example of the bonded portions, in which FIG. 12(a) is a plan view, and FIG. 12(b) is a cross-sectional view taken along line B-B.

FIG. 13 is a plan view illustrating an arrangement example of the bonded portions.

FIG. 14 is a plan view illustrating an arrangement example of the bonded portions.

FIG. 15 is a plan view illustrating an arrangement example of the bonded portions.

FIG. 16 is a plan view illustrating an arrangement example of the bonded portions.

FIG. 17 is a plan view illustrating an arrangement example of the bonded portions.

FIG. 18 is a plan view illustrating an arrangement example of the bonded portions.

FIG. 19 is a plan view illustrating an arrangement example of the bonded portions.

FIG. 20 is an explanatory diagram of a shape example of the bonded portions.

FIG. 21 is a cross-sectional view illustrating a bonding form example at the bonded portions.

FIG. 22 is a cross-sectional view illustrating a bonding form example at the bonded portions.

FIG. 23 is a plan view illustrating a bonding form example.

FIG. 24 is a schematic view of an ultrasonic sealing device.

FIG. 25 is a comparative explanatory diagram of an arrangement example of the bonded portions.

FIG. 26 is a comparison diagram illustrating (a) a spread state, (b) a natural length state, and (c) a worn state of the underpants-type disposable diaper in comparison.

FIG. 27 is a comparison diagram illustrating (a) a spread state, (b) a natural length state, and (c) a worn state of the underpants-type disposable diaper in comparison.

FIG. 28 is a plan view illustrating a main part of the underpants-type disposable diaper in the spread state.

FIG. 29 is a plan view (internal surface side) of the underpants-type disposable diaper in the spread state.

FIG. 30(a) is a cross-sectional view taken along line C-C of FIG. 29, and FIG. 30(b) is a cross-sectional view taken along line E-E of FIG. 29.

DESCRIPTION OF EMBODIMENTS

Hereinafter, an example of an underpants-type disposable diaper will be referred to describe a disposable wearable article in detail with reference to the accompanying drawings. Note that a dotted pattern portion in the figures indicates an adhesive as bonding means that bonds respective components located on the front surface side and the back surface side thereof, and is formed by solid, bead, curtain, summit, or spiral coating of a hot melt adhesive, or pattern coating (transfer of the hot melt adhesive in a letterpress method), or application of an elastic member to an outer peripheral surface such as comb gun or sure wrap application instead of or together with the above methods in a fixed part of the elastic member. Examples of the hot melt adhesive include EVA-based, pressure sensitive adhesion rubber-based (elastomer-based), polyolefin-based, and polyester/polyamide-based adhesives, and can be used without any particular limitation. As bonding means that bonds respective components, it is possible to use means by material welding such as heat sealing or ultrasonic sealing.

FIGS. 1 to 6 illustrate the underpants-type disposable diaper (hereinafter also simply referred to as a diaper) as an example of the disposable wearable article. Reference character ED indicates a stretchable direction ED of a stretchable region, which is the same direction as a width direction WD of the diaper in this example. Reference character XD indicates a direction orthogonal to the stretchable direction ED, which is the same direction as a front-back direction LD of the diaper in this example.

The underpants-type disposable diaper has an outer body 20 forming a front body F and a back body B, and an inner body 10 fixed to and integrated with an inner surface of the outer body 20, and the inner body 10 is obtained by interposing an absorber 13 between a liquid pervious top sheet 11 and a liquid impervious sheet 12. In manufacturing, after a back surface of the inner body 10 is bonded to an inner surface (upper surface) of the outer body 20 by bonding means such as a hot melt adhesive, the inner body 10 and the outer body 20 are folded at a center in a front-back direction LD (vertical direction), which is a boundary between the front body F and the back body B, and both side portions thereof are bonded by heat welding or a hot melt adhesive to form side seal portions 21, thereby forming the underpants-type disposable diaper in which a waist opening and a pair of right and left leg openings are formed.

(Example of Structure of Inner Body)

As illustrated in FIGS. 4 to 6, the inner body 10 has a structure in which the absorber 13 is interposed between the liquid pervious top sheet 11 and the liquid impervious sheet 12 made of polyethylene, etc., and absorbs and retains an excreted liquid passing through the top sheet 11. A planar shape of the inner body 10 is not particularly limited, and is generally a substantially rectangular shape as illustrated in FIG. 1.

As the top sheet 11 that covers the front surface side (skin side) of the absorber 13, a perforated or non-perforated nonwoven fabric, a porous plastic sheet, etc. is preferably used. As a raw material fiber included in the nonwoven fiber, in addition to synthetic fibers such as polyolefin-based fiber such as polyethylene or polypropylene, polyester-based fiber, and polyamide-based fiber, it is possible to use regenerated fibers such as rayon and cupra, and natural fibers such as cotton, and it is possible to use a nonwoven fabric obtained by an appropriate processing method such as a spun lace method, a spun bond method, a thermal bond method, a melt blown method, or a needle punch method. Among these processing methods, the spun lace method is excellent in flexibility and drapability, and the thermal bond method is excellent in bulkiness and softness. When a plurality of through holes are formed in the top sheet 11, urine and, etc. can be rapidly absorbed, and a dry touch property becomes excellent. The top sheet 11 extends up to the back surface side of the absorber 13 with side edge portions of the absorber 13 wrapped around.

As the liquid impervious sheet 12 covering the back surface side of the absorber 13 (non-skin contact side), a liquid impervious plastic sheet of polyethylene, polypropylene, etc. is used. However, in recent years, a sheet having moisture permeability is preferably used from a viewpoint of preventing stuffiness. This water blocking and moisture-permeable sheet is, for example, a microporous sheet obtained by melt kneading an inorganic filler in a polyolefin resin such as polyethylene or polypropylene to form a sheet, and then monoaxially or biaxially stretching the sheet.

As the absorber 13, it is possible to use a known one, for example, an accumulates of pulp fibers, an assembly of filaments such as cellulose acetate, or one having a nonwoven fabric as a base and a super absorbent polymer mixed and fixed therein as necessary. The absorber 13 can be wrapped with a wrapping sheet 14 such as crepe paper having the liquid pervious property and liquid holding property to hold the shape and the polymer as necessary.

A shape of the absorber 13 can be a substantially hour-glass shape having a narrowing part 13N narrower than both front and back sides in a crotch portion. Dimensions of the narrowing part 13N can be appropriately determined. However, a front-back direction dimension of the narrowing part 13N can be set to about 20 to 50% of a maximum length of the diaper, and a width of a narrowest part thereof can be set to about 40 to 60% of a maximum width of the absorber 13. In the case of having such a narrowing part 13N, when the planar shape of the inner body 10 is substantially rectangular, a non-absorber side portion 17 not having the absorber 13 is formed in a part of the inner body 10 corresponding to the narrowing part 13N of the absorber 13.

The liquid impervious sheet 12 is folded back to the back surface side together with the top sheet 11 on both sides of the absorber 13 in the width direction. As the liquid impervious sheet 12, it is desirable to use an opaque sheet so that brown of excreta, urine, etc. does not appear. As the opaque sheet, a film obtained by internally adding a pigment or a filler such as calcium carbonate, titanium oxide, zinc oxide, white carbon, clay, talc or barium sulfate to plastic is preferably used.

Three-dimensional gathers 90 fit around legs are formed on both sides of the inner body 10. As illustrated in FIGS. 5 and 6, each of the three-dimensional gathers 90 has fixed portion 91 fixed to a side portion of a back surface of the inner body 10, a main unit section 92 extending from the fixed portion 91 to a side portion on a front surface of the inner body 10 through a side of the inner body 10, a fallen portion 93 formed by fixing front and back end portions of the main unit section 92 to the side portion of the front surface of the inner body 10 (top sheet 11 in the illustrated embodiment) in a fallen state, and a free part 94 formed by not fixing between fallen portions 93. Each of these portions is formed by a gather sheet 95 that is a duplicate sheet obtained by folding back a sheet of a nonwoven fabric, etc. The gather sheet 95 is attached over the entire part of the inner body 10 in the front-back direction, the fallen portion 93 is provided on the front side and the back side of the non-absorber side portion 17, and the free part 94 extends on both front and back sides of the non-absorber side portion 17. In addition, an elongated gather elastic member 96 is arranged at a tip portion of the free part between parts of the double gather sheet 95. The gather elastic member 96 is for raising the free part 94 by elastic contraction force as illustrated in FIG. 5 in a product state.

In the embodiment illustrated in FIGS. 5 and 6, in a part other than the fallen portion 93, the gather elastic member 96 is attached and fixed to the gather sheet 95 through a hot melt adhesive at a position of the gather elastic member 96, and facing surfaces of the gather sheet 95 are not bonded. However, in the fallen portion 93, there is no hot melt adhesive at the position of the gather elastic member 96, and therefore the gather elastic member 96 and the gather sheet 95 are not bonded, and the facing surfaces of the gather sheet 95 are not bonded at a position having the gather elastic member 96.

The three-dimensional gathers 90 illustrated in FIGS. 5 and 6 correspond to a mode in which the main unit sections 92 are not folded back.

Examples of the gather elastic member 96 include a commonly used material such as polystyrene-based rubber, polyolefin-based rubber, polyurethane-based rubber, polyester-based rubber, polyurethane, polyethylene, polystyrene, styrene-butadiene copolymer, silicone, or polyester. Further, in order to make it difficult to see from the outside, it is preferable that the thickness is 925 dtex or less, the tension is 150 to 350%, and the interval is 7.0 mm or less. Note that as the gather elastic member 96, in addition to a thread-shaped member as in the illustrated embodiment, it is possible to use a tape-shaped member having a certain width.

As a row material fiber included in the gather sheet 95, similarly to the top sheet 11, in addition to synthetic fibers such as polyolefin-based fiber such as polyethylene or polypropylene, polyester-based fiber, and polyamide-based fiber, it is possible to use regenerated fibers such as rayon and cupra, and natural fibers such as cotton, and it is possible to use a nonwoven fabric obtained by an appropriate processing method such as a spun bond method, a thermal bond method, a melt blown method, or a needle punch method. In particular, in order to prevent stuffiness, it is preferable to use a nonwoven fabric having a low basis weight and excellent air permeability. Further, with regard to the gather sheet 95, in order to prevent the permeation of urine, etc., prevent the rash, and enhance the texture (dry feeling), it is desirable to use a water-repellent nonwoven fabric coated with a silicone-based, paraffin metal-based, or alkylchromic chloride-based water repellent agent.

As illustrated in FIGS. 3 to 6, the back surface of the inner body 10 is bonded to the inner surface of the outer body 20 by a hot melt adhesive, etc. in an inner/outer fixing region 10B (diagonal line region). The inner/outer fixing region 10B can be appropriately determined and can be set to almost the entire part of the inner body 10 in the width direction WD, and it is preferable that both end portions in the width direction are not fixed to the outer body 20.

(Example of Structure of Outer Body)

The outer body 20 extends outward from side edges of the absorber 13. Referring to the outer body 20, side edges of the outer body 20 may be located on the center side of side edges of the inner body 10 in the width direction in the crotch portion as in the illustrated embodiment, or located on the outer side thereof in the width direction. In addition, the outer body 20 has a lower torso portion T which is a front-back direction range corresponding to the side seal portions 21 and an intermediate portion L which is a front-back direction range between the lower torso portion T of the front body F and the lower torso portion T of the back body B. A planar shape of the outer body 20 is formed by concave around-leg lines 29 so that both side edges of the intermediate portion L in the width direction form leg openings, respectively, and forms a shape similar to an hourglass as a whole. The outer body 20 may be separately formed in the front body F and the back body B, and both parts may be arranged to be separated in the front-back direction LD of the diaper in the crotch portion.

Further, except for a middle of the intermediate portion L in the front-back direction, the outer body 20 of the illustrated embodiment has an elastic sheet stretchable structure 20X in which an elastic sheet 30 such as an elastic film is interposed between the first sheet layer 20A and the second sheet layer 20B as illustrated in FIG. 2 and FIGS. 4 to 6, and the first sheet layer 20A and the second sheet layer 20B are bonded through joint holes 31 penetrating the elastic sheet 30 at a plurality of bonded portions 40 arranged at intervals as illustrated in FIG. 9. In this case, the stretchable direction ED is the width direction WD of the diaper. The first sheet layer 20A and the second sheet layer 20B may be indirectly bonded via the elastic sheet 30 instead of through the joint holes 31 of the elastic sheet 30.

The mode illustrated in FIGS. 1 and 2 is a mode in which the elastic sheet stretchable structure 20X is extended to waist end portions 23. However, when the elastic sheet stretchable structure 20X is used in the waist end portions 23, tightening of the waist end portions 23 is insufficient. As necessary, as illustrated in FIGS. 7 and 8, instead of providing the elastic sheet stretchable structure 20X in the waist end portions 23, it is possible to provide a stretchable structure by conventional elongated waist portion elastic members 24. The waist portion elastic members 24 are elongated elastic members such as a plurality of rubber threads arranged at intervals in the front-back direction LD, and gives a stretching force so as to tighten around a waist of a body. The waist portion elastic members 24 may not be arranged closely substantially in a bundle, and three or more, preferably five or more waist portion elastic members 24 are arranged at intervals of about 3 to 8 mm in the front-back direction to form a predetermined stretchable zone. A stretch rate of the waist portion elastic members 24 during fixing can be appropriately determined. However, in the case of using for normal adults, the stretch rate can be set to about 230 to 320%. The waist portion elastic members 24 are made of rubber threads in the illustrated example. However, for example, it is possible to use other elongated elastic members such as flat rubbers. Although not illustrated, it is possible to provide the elastic sheet 30 in the waist end portions 23, and provide the elongated waist portion elastic members 24 at positions overlapping the elastic sheet 30, thereby forming a stretchable structure by both the elastic members. In addition, in the illustrated embodiment, the elongated elastic members extending along the leg openings are not provided at edge parts of the leg openings in the outer body 20. However, it is possible to provide elongated elastic members at positions of the edge parts overlapping the elastic sheet 30 or in place of the elastic sheet 30 at the edge parts.

As another mode, although not illustrated, it is possible to adopt a mode in which the elastic sheet stretchable structure 20X is not provided to the intermediate portion L between the lower torso portion T of the front body F and the lower torso portion T of the back body B, or an appropriate modification in which the elastic sheet stretchable structure 20X is provided continuously in the front-back direction LD from the inside of the lower torso portion T of the front body F to the inside of the lower torso portion T of the back body B through the intermediate portion L, or the elastic sheet stretchable structure 20X is provided only to one of the front body F and the back body B.

(Cover Sheet)

As illustrated in FIGS. 29 and 30, cover sheets 50 and 60 are provided to reinforce the outer body 20 or cover front and back end portions of the inner body 10 attached to the inner surface of the outer body 20. The illustrated embodiment will be more specifically described. The cover sheet 50 on the front side extends over the entire part in the width direction WD from an inner surface of a folded part 20C on the waist side in the inner surface of the front body F to a position overlapping the front end portion of the inner body 10, and the cover sheet 60 on the back side extends over the entire part in the width direction WD from the inner surface of the folded part 20C on the waist side in the inner surface of the back body B to a position overlapping the back end portion of the inner body 10. Bonding between the cover sheets 50 and 60 and the inner surface of the outer body 20, that is, the inner surface of the first sheet layer 20A in the illustrated example can be performed by a hot melt adhesive or by material welding. When a slight non-bonded portion is provided over the entire part in the width direction WD (or may be provided only at a center portion) at a crotch side edge portion of each of the cover sheets 50 and 60, this portion can be slightly lifted from the top sheet 11 to function as a leak prevention wall.

When the cover sheets 50 and 60 are separately attached as in the illustrated embodiment, there is an advantage that a degree of freedom in selecting a material is increased. However, there is a demerit that the number of materials and the manufacturing process are increased. For this reason, the folded part 20C obtained by folding back the outer body 20 on the inner surface of the diaper can be extended to the part overlapping the inner body 10 to form a part equivalent to the above-described cover sheets 50 and 60 (not illustrated).

(Stretchable Region)

A region of the outer body 20 having the elastic sheet stretchable structure 20X has a stretchable region that can be extended and contracted in the width direction WD. In a stretchable region 80, the elastic sheet 30 has a part 32 (see FIG. 12(a)) that is linearly continuous along the width direction WD, contracts in the width direction WD by a contraction force of the elastic sheet 30, and is stretchable in the width direction WD. More specifically, in a state where the elastic sheet 30 is extended in the width direction WD, the first sheet layer 20A and the second sheet layer 20B are bonded through the joint holes 31 of the elastic sheet 30 at intervals in the width direction WD and the front-back direction LD orthogonal thereto (direction LD orthogonal to the stretchable direction), and the plurality of bonded portions 40 is formed, thereby forming the elastic sheet stretchable structure 20X. Further, in the stretchable region 80, such elasticity can be imparted by arranging the joint holes 31 so that the elastic sheet 30 has the part 32 (see FIG. 12(a)) that is linearly continuous along the width direction WD.

The stretchable region 80 may have a part (separation interval d described later) in which the elastic sheet 30 is linearly continuous along the width direction WD as in an example illustrated in FIG. 25(a) described later or may not have the part as in an example illustrated in FIG. 25(b).

In the natural length state, as illustrated in FIGS. 9 and 12(b), the stretchable region 80 bulges in a direction in which the first sheet layer 20A and the second sheet layer 20B between the bonded portions 40 are separated from each other, and pleats 25F extending in the front-back direction LD are formed. Even in a worn state of extending in the width direction WD to some extent, the pleats 25F are left even though the pleats 25F are stretched. In addition, as in the illustrated example, when the first sheet layer 20A and the second sheet layer 20B are not bonded to the elastic sheet 30 except at least between the first sheet layer 20A and the second sheet layer 20B in the bonded portions 40, as can be seen from FIG. 9(c) presuming the worn state and FIG. 9(a) presuming a spread state of the first sheet layer 20A and the second sheet layer 20B, in these states, a gap is formed between the joint holes 31 in the elastic sheet 30 and the bonded portions 40, and air permeability is imparted by this gap even when the material of the elastic sheet 30 is a non-perforated film or sheet. In addition, in the natural length state, the joint holes 31 are narrowed by further contraction of the elastic sheet 30, and almost no gap is formed between the joint holes 31 and the bonded portions 40.

It is desirable that elongation at elastic limit of the stretchable region 80 in the width direction WD is set to 190% or more (preferably 225 to 285%). The elongation at elastic limit of the stretchable region 80 decreases due to a factor that inhibits contraction in the width direction WD based on a stretch rate of the elastic sheet 30 at the time of manufacturing. In a normal case, a length L of the bonded portions 40 has a correlation with an area ratio of the bonded portions 40, and thus the elongation at elastic limit of the stretchable region 80 can be adjusted by the area ratio of the bonded portions 40.

Where the elastic sheet 30 has the part (separation interval d described later) which is linearly continuous along the width direction WD as in the example illustrated in FIG. 25(a) described later, the extension stress of the stretchable region 80 can be adjusted mainly by a sum of orthogonal direction dimensions (equal to the separation interval d of the joint holes 31) of the part in which the elastic sheet 30 is linearly continuous along the width direction WD. On the other hand, where the elastic sheet 30 has not the part which is linearly continuous along the width direction WD as in the example illustrated in FIG. 25(b), the extension stress can be adjusted by an angle γ described later. In a normal case, it is preferable that the angle γ is set to a range of more than 0 degree and 45 degrees or less, particularly to a range of 10 to 30 degrees.

The area ratio of the bonded portions 40 and the area of each of the bonded portions 40 in the stretchable region 80 can be appropriately determined. However, in the normal case, the area ratio and the area are preferably within the following ranges.

Area of each of bonded portions 40: 0.14 to 3.5 mm² (especially 0.14 to 1.0 mm²)

Area ratio of bonded portions 40: 1.8 to 19.1% (especially 1.8 to 10.6%)

In this way, since the elongation at elastic limit and the extension stress of the stretchable region 80 can be adjusted by the area of the bonded portions 40, as illustrated in FIG. 7, a plurality of regions having different area ratios of the bonded portions 40 can be provided in the stretchable region 80 to change fitting depending on the site. In an example illustrated in FIG. 7, edge portion stretchable regions 82 of the leg openings are provided, and the edge portion stretchable regions 82 are set to flexibly extending and contracting regions in which the area ratio of the bonded portions 40 is higher than that of other regions, and thus the extension stress is weak.

A shape of each of the bonded portions 40 and the joint holes 31 in the natural length state can be appropriately determined, and can be set to an arbitrary shape such as a perfect circle, an ellipse (see FIG. 20(d)), a polygon such as a triangle, a rectangle (see FIG. 9, etc.), or a rhombus (see FIG. 20(b)), a convex lens shape (see FIG. 20(a)), a concave lens shape (see FIG. 20(c)), a star shape, or a cloud shape. Dimensions of each of the bonded portions 40 are not particularly limited. However, a maximum length 40y (almost equal to the dimension 31y of the joint holes 31 in the orthogonal direction) is preferably 0.5 to 3.0 mm, particularly 0.7 to 1.1 mm, and a maximum width 40x is preferably 0.1 to 3.0 mm, particularly 0.1 to 1.1 mm in the case of a shape which is long in the direction XD orthogonal to the stretchable direction.

The joint holes 31 mainly relate to the shape of the bonded portions 40 (41, 42, and 43) and a manufacturing stage or a degree of extension and contraction.

Hereinafter, arrangement examples of the bonded portions suitable for the stretchable region will be described in order.

(Arrangement Example 1 of Bonded Portions)

FIG. 9 is illustrated as a representative example in Patent Literature 1. That is, a group of the bonded portions 40 is in staggered arrangement, the bonded portions 40 have a line-symmetrical shape (right-left symmetry in FIG. 9(a)) with respect to a center line passing through a center in the stretchable direction, which is elongated in the direction orthogonal to the stretchable direction, the width 40x of the bonded portions 40 in the stretchable direction is preferably set to 0.2 to 0.4 mm, an interval d1 of the bonded portions 40 arranged in the stretchable direction is set to 3 to 12.9 mm, more preferably 5 to 6.4 mm, and an interval d2 of the bonded portions 40 arranged in the direction orthogonal to the stretchable direction is set to 2 to 10.5 mm, more preferably 2.3 to 4.6 mm.

In this way, the bonded portions 40 having a remarkably narrow width 40x in the stretchable direction are arranged in a staggered shape at the separation interval d1 which is wide to some extent in the stretchable direction, the contraction force of the elastic sheet 30 directly acts on each of the bonded portions 40, and arrangement/interval of the respective bonded portions 40 are firmly maintained at positions of the joint holes 31 of the elastic sheet 30. As a result, flexibility is less likely to deteriorate. In addition, pleats 25f extend almost straight along the direction orthogonal to the stretchable direction, and the bonded portions 40 are hidden between the pleats 25f and the pleats 25f and become inconspicuous. Therefore, the elastic sheet stretchable structure 20X has an appearance closer to that of cloth while suppressing deterioration in flexibility.

On the other hand, even though arrangement of the bonded portions 40 is staggered arrangement, when the shape of each of the bonded portions 40 is a circular shape, the bonded portions 40 are clearly visible between the pleats 25f and the pleats 25f which are wrinkles, and the pleats 25f greatly wrap around the bonded portions 40 and extend in the direction orthogonal to the stretchable direction. Thus, the wavy line-shaped pleats 25f are formed as a whole, and cloth-like appearance is less likely to be obtained.

From this point of view, it is desirable that the shape of each of the bonded portions 40 is elongated in the direction orthogonal to the stretchable direction. However, when the maximum length of the bonded portions 40 in the direction orthogonal to the stretchable direction is excessively short or excessively long, there is concern that linearity of the pleats 25f may decrease, or flexibility may decrease. Therefore, these dimensions can be appropriately determined. However, it is preferable that the length 40y of the bonded portions 40 in the direction orthogonal to the stretchable direction is 0.4 to 3.2 mm, and particularly 0.7 to 1.4 mm.

Meanwhile, in Patent Literature 2, in both examples of FIG. 10(a)(b), arrangement of bonded portions of an elastic film (illustrated as a rather vertically long rectangle) is similarly staggered arrangement, and in the example of FIG. 10(b), small circular sub-bonded portions are arranged between rectangular main bonded portions. The example of FIG. 10(b) is based on the idea of staggered arrangement.

Further, arrangement and dimensions of the respective bonded portions are preferably within dimensional ranges (unit is mm) illustrated in FIG. 10 mainly in terms of appearance, touch, and air permeability.

(Arrangement Example 2 of Bonded Portions)

In arrangement example 1 described above, the separation interval between the bonded portions of the elastic sheet 30 in the direction orthogonal to the stretchable direction, which is reference character C in FIG. 10(a), is set to be a large value of 0.3 mm or more, and thus stretching stress in the stretchable direction is high. For example, in the case of applying to the underpants type disposable diaper, there are not a few wearers who feel that the wearers are excessively tightened (in the width direction).

Here, in Patent Literature 2, it is preferable that a length B of the bonded portions illustrated in FIG. 10 is 0.3 to 0.7 mm, and a separation interval H is 0.6 to 1.4 mm.

On the other hand, as illustrated in FIG. 11, when the separation interval d between the bonded portions of the elastic sheet 30 in the orthogonal direction XD orthogonal to the stretchable direction ED is set to be small, the stretching stress in the stretchable direction can be reduced. Therefore, in the case of applying to the underpants-type disposable diaper, the disposable diaper can be gently fit to the wearer with a weak tightening force.

A reason therefor is considered as follows. While the bonded portions are open in the width direction and become the joint holes 31 as illustrated in FIG. 9 merely by applying a small stretching force in the width direction (stretchable direction of the elastic sheet 30) from the outside, the bonded portions are not present in a separation interval region orthogonal to the stretchable direction between the bonded portions even when stretched in the width direction. Thus, the extension stress of the elastic sheet 30 becomes a contraction force without change to tighten the wearer.

The mode illustrated in FIG. 11 has an advantage that the diaper can be gently fit to the wearer, and air permeability is excellent since an area ratio of the bonded portions and an area ratio of the joint holes in a use state of being stretched in the width direction increase.

(Arrangement Example 3 of Bonded Portions)

Arrangement example 2 described above has an advantage that the diaper can be gently fit to the wearer. However, it may be desirable to apply a weaker contraction force.

In addition, a product provider generally sets a wearer having an intermediate body type within a certain body type (size around the waist) group range and determines the contraction force of the diaper for the wearer.

There are large individual differences in the size around the waist, and there is a desire for a product in which the contraction force of the diaper with respect to the wearer does not change much between a person having a large waist and a person having a thin waist as much as possible.

FIG. 25 illustrates one possible solution to this problem. In more detail, in an example illustrated in FIG. 25, in the stretchable region, the bonded portions 40 are formed to be spaced apart in the stretchable direction ED and the orthogonal direction XD orthogonal thereto, a group of the bonded portions 40, 40 . . . in the stretchable region is in a relationship of intersecting a stretchable direction line at each position in the orthogonal direction XD as in FIG. 25(b) or in a relationship of not intersecting the stretchable direction line at a separation width of 0.5 mm or less in the orthogonal direction XD of the stretchable direction line as in FIG. 25(c), and at a predetermined orthogonal direction XD separation width in an orthogonal direction XD diagonal line group of diagonal lines q intersecting the stretchable direction line within a range of an angle γ of 45 degrees or less (that is, a diagonal line group between the diagonal lines q and q of FIG. 25(b)), the bonded portion group is in a relationship not intersecting the diagonal lines.

A reason why this example does not give an excessive contraction force to the wearer is presumed to be due to the following phenomenon even though the reason may not be clear.

It is considered that stretching in the stretchable direction may not occur when the bonded portion group is in the relationship of intersecting the stretchable direction line at each position in the orthogonal direction XD as in FIG. 25(b), or is in a relationship of not intersecting the stretchable direction line at the separation interval d of 0.5 mm or less in the orthogonal direction XD of the stretchable direction line as in FIG. 25(c).

However, a force in the stretchable direction in the case of spreading in the stretchable direction ED during wearing is propagated while making a detour as in FIG. 25(b) (a propagation path is indicated by reference character S). The propagation path S is illustrated since the elastic sheet 30 extends and contracts in the orthogonal direction in addition to the width direction. As a result, extension in the stretchable direction ED occurs while forming the joint holes 31 and 31 on both sides of the bonded portion 40 in the width direction.

In general, when the elastic sheet 30 is stretched during manufacturing, and then a stretching force is released, the elastic sheet 30 does not return to an original length and returns to a length obtained by subtracting strain. For example, when an elastic sheet having a natural length of 50 mm is stretched 3.5 times to 175 mm and a stretching force is released to 70 mm, there is a strain of 20 mm, and a strain ratio ε % is (70−50)×100/50=40%.

Based on this fact, when further studied, in the spread state of the diaper in the width direction, stretching in the stretchable direction occurs while forming the joint holes 31 and 31 on both sides of the bonded portion 40 in the width direction. That is, the elastic sheet is deformed on both sides of the bonded portion 40 in the width direction by the openings of the joint holes 31 and 31. It will be understood that the part that has once deformed has a smaller contraction force.

In this way, when a spreading force of the diaper is released, contraction in the width direction occurs while shorting an opening width (opening length) of the joint holes 31 and 31 by the contraction force of the elastic sheet. In this case, when the separation interval d is large, the elastic sheet is not deformed in a separation interval d region, and thus the amount (length) of contraction in the width direction is large. For example, in the case of a thin person, contraction occurs until the joint holes 31 and 31 are closed. As a result, there is concern that air permeability from the openings of the joint holes 31 and 31 may be insufficiently ensured.

On the other hand, when the separation interval d is small or zero, the elastic sheet 30 is deformed by the openings of the joint holes 31 and 31 (in a sense, the elastic sheet is damaged) in the all part or almost all part in the orthogonal direction. As a result, when the stretching force in the width direction is released, the opening width (opening length) of the joint holes 31 and 31 that have been once opened is short and a ratio thereof is small. Therefore, ensuring of the air permeability from the openings of the joint holes 31 and 31 is not excessively reduced.

Moreover, the contraction force in the width direction is smaller than that in a case where the separation interval d is large, and thus the wearer is not excessively pressed.

Note that, for example, to cause extension and contraction in the width direction in the propagation path S, as illustrated in FIG. 25(b), at a predetermined separation interval H in the orthogonal direction XD in a orthogonal direction diagonal line group of the diagonal lines q and q intersecting the stretchable direction line within the range of the angle γ of 45 degrees or less, the group of bonded portions 40, 40 . . . needs to be in a relationship not intersecting the diagonal lines.

Here, for example, as illustrated in FIG. 17, the angle γ of 45 degrees or less with respect to the stretchable direction line is defined as an opening angle between the stretchable direction line and the diagonal line q even in the case of a diagonal line from the upper left to the lower right.

The separation interval H along the orthogonal direction XD is 0.2 to 10 mm, more desirably 0.2 to 5.0 mm, and particularly desirably 0.6 to 3.0 mm.

The opening angle γ between the stretchable direction line and the diagonal line is more preferably 30 degrees or less, and particularly desirably 15 degrees or less.

The bonded portions 40 are formed to have a stretchable direction width of 0.3 to 10.0 mm, preferably 0.5 to 5.0 mm, and particularly preferably 0.7 to 3.5 mm.

The bonded portions 40 are formed to have a length L based on the orthogonal direction XD in a range of 0.3 to 7.0 mm, preferably 0.5 to 5.0 mm, and particularly preferably 0.7 to 2.5 mm.

In addition, a row of first bonded portions 40, 40 . . . is formed to have a forming pitch S0 based on the stretchable direction ED (WD) in a range of 2.0 to 20.0 mm, preferably 3.0 to 15.0 mm, and particularly preferably 4.0 to 10.0 mm.

Hereinafter, various modifications based on the above-mentioned arrangement example 3 will be described in order.

(Arrangement Example 4 of Bonded Portions)

In a usage form of a product having a form illustrated in FIG. 12(a), the pleats 25F along the orthogonal direction XD are formed in a separation region between a row of bonded portions 40, 40 . . . along the orthogonal direction XD and a row of adjacent bonded portions 40, 40 . . . spaced apart therefrom in the stretchable direction ED. As illustrated in FIG. 12(b), the pleats 25F simply have a uniform mountain shape. That is, the shape is different from that in the cross section shown in Patent Literature 1 and illustrated here in FIG. 9(c).

The example illustrated in FIG. 12 has the elastic sheet stretchable structure in which the elastic sheet is interposed between the first sheet layer having air permeability and the second sheet layer having air permeability, and the first sheet layer and the second sheet layer are bonded through the joint holes penetrating the elastic sheet or with the elastic sheet interposed therebetween at a plurality of bonded portions arranged at intervals.

In addition, the stretchable region exhibiting the elastic sheet stretchable structure can be extended and contracted in the stretchable direction by the contraction force of the elastic sheet.

The bonded portions have second bonded portions 41, 41 . . . in addition to the first bonded portions 40, 40 . . . .

The first bonded portions 40, 40 . . . are arranged at intervals along the orthogonal direction XD, and a first bonded portion row is formed.

As will be described later with reference to FIG. 19, for example, the row of the first bonded portions 40, 40 . . . does not extend along the orthogonal direction XD and is inclined in a range in which an angle θ intersecting the stretchable direction ED is 30 degrees to 150 degrees (therefore 90 degrees is not included), and is more desirably inclined in a range of 45 degrees to 135 degrees (90 degrees is not included).

In the example illustrated in FIG. 12, the angle θ at which inclination does not occur and intersection occurs is 90 degrees.

The first bonded portions 40 are formed to have a length L based on the orthogonal direction XD in a rage of 0.3 to 7.0 mm, preferably 0.5 to 5.0 mm, and particularly preferably 0.7 to 2.5 mm.

In addition, a row of first bonded portions 40, 40 . . . is formed to have a forming pitch S0 based on the stretchable direction ED (WD) in a range of 2.0 to 20.0 mm, preferably 3.0 to 15.0 mm, and particularly preferably 4.0 to 10.0 mm.

Further, as a distance based on the orthogonal direction XD, which is determined by a mutual relationship between the adjacent first bonded portions 40 and 40 in the row of the first bonded portions 40, 40 . . . , a percentage R of a ratio of (separation distance d between adjacent first bonded portions)/(distance P from a point of the bonded portions to a point corresponding to an adjacent first bonded portion) is desirably set to 5 to 60%, preferably 10 to 45%, and particularly 20 to 35%.

When this percentage is excessively high, in the case of being applied to a product, the stretching stress in the width direction (stretchable direction) is high, and it tends to be difficult to obtain suitable fitting as a wearable article.

In addition, when the percentage is excessively low, it is impossible to exclude the possibility that the first bonded portions 40 and 40 adjacent to each other in the orthogonal direction XD may become mutually continuous in a manufacturing process. More fundamentally, an anvil and a heating horn that form the bonded portions may have an excessive facility load, which may hinder stable operation.

It is desirable that a bonded portion having the length L of the first bonded portions 40 or a larger length is not formed in the row of the second bonded portions 41 and 41.

In this example, the following advantages or characteristics are typically shown.

(1) Since the above-mentioned percentage R is low, the elastic sheet member has a low stretching stress in the stretchable direction and has a flexible elongation, and when this elastic sheet member is applied to an absorbent article, wearing feeling becomes excellent.

Moreover, since an opening ratio becomes high, the air permeability becomes high.

(2) Since not only the row of the first bonded portions 40, 40 . . . , but also the row of the second bonded portions 41, 41 . . . is formed, an inter-row pleat R can be formed between the row of the first bonded portions 40, 40 . . . and the row of the second bonded portions 41, 41 . . . . In the form illustrated in FIG. 11, from a viewpoint of design as the entire stretchable region of the product, the pleats 25F which are long in the orthogonal direction XD are formed in a uniform repeat in the stretchable direction ED (WD). On the other hand, in this example, a design property can be enhanced by forming the inter-row pleat R.

(3) The second bonded portions 41 have a smaller area than that of the first bonded portions 40, and thus look like a pattern.

(4) The fact that the inter-row pleat R can be formed between the row of the first bonded portions 40, 40 . . . and the row of the second bonded portions 41, 41 . . . means that two inter-row pleats can be formed between the row of the first bonded portions 40, 40 . . . and the row of the first bonded portions 40, 40 . . . . However, in the row of the second bonded portions 41, 41 . . . , an interval between the second bonded portions 41 and 41 is long, and thus the fact means that the pleats can be formed without an excessive facility load applied to the anvil and the heating horn. As a result, when compared to the case of forming the inter-row pleats only by the row of the first bonded portions 40, 40 . . . as in FIG. 11, a plurality of pleats having narrow widths per unit area can be formed without applying the facility load. In this way, the contact area on the skin of the wearer is reduced, and comfort and softness can be improved.

(Arrangement Example 5 of Bonded Portions)

As illustrated in FIG. 13, the group of the second bonded portions 41, 41 . . . can be arranged between the first bonded portions 40 and 40 in the orthogonal direction XD. In this case, even when the length L of the first bonded portion 40 is short, the stretching stress can be reduced since the second bonded portions 41 are positioned.

(Arrangement Example 6 of Bonded Portions)

As illustrated in FIG. 14, the second bonded portions 41 may not be adjacent to the first bonded portions 40 on a one-to-one basis. For example, it is possible to adopt a mode in which one second bonded portion 41 is arranged to be adjacent to two first bonded portions 40 and 40.

(Arrangement Example 7 of Bonded Portions)

As illustrated in FIG. 15, a row of third bonded portions 42, 42 . . . having a long separation interval in the orthogonal direction XD can be formed between the row of the first bonded portions 40, 40 . . . and the row of the second bonded portions 41, 41 . . . . By forming the third bonded portion 42, it is possible to form a large pleat bf obtained by dividing the inter-row pleat R illustrated in a first embodiment in the orthogonal direction XD. A small pleat sf can be formed between the third bonded portion 42 and the row of the first bonded portions 40, 40 . . . . A group of pleats formed by dividing the inter-row pleat R lowers flexural rigidity of the stretchable member (easy to bend) and has excellent followability to movement of the body.

(Arrangement Example 8 of Bonded Portions)

As illustrated in FIG. 16, by obliquely arranging positions of the third bonded portions 42 together with the second bonded portions 41, a group of large pleats bf in oblique arrangement can be formed, and a design property is enhanced.

(Arrangement Example 9 of Bonded Portions)

As illustrated in FIG. 17, a fourth bonded portion 43 can be arranged to be inserted into the row of the first bonded portions 40, 40 . . . . In this case, a group of the fourth bonded portions 43, 43 . . . extends along the stretchable direction ED, and can be obliquely arranged as illustrated in the figure. In this case, the area of the fourth bonded portion 43 is preferably 5% or more and 50% or less of the area of the first bonded portion 40.

(Arrangement Example 10 of Bonded Portions)

As illustrated in FIG. 18, the first bonded portion 40 may be inclined. The second bonded portion 42 may be inclined. Since the bonded portion length is based on the orthogonal direction XD, as illustrated in FIG. 18, the length L of the first bonded portion 40 is a bonded portion length corresponding to a length in the orthogonal direction XD from a center of one side to a center portion of the other side. As for the separation interval, a distance in the orthogonal direction XD between a center of a side and a center of an opposite side is a separation distance d.

(Arrangement Example 11 of Bonded Portions)

FIG. 19 illustrates an example in which both the first bonded portions 40 and the second bonded portions 42 are inclined, and each of the row of the first bonded portions 40 and the row of the second bonded portions 42 does not extend along the orthogonal direction XD and is inclined in a range in which the angle θ intersecting the stretchable direction ED is 30 degrees to 150 degrees, desirably 45 degrees to 135 degrees. The intersecting angle θ is particularly preferably 60 degrees to 120 degrees. However, 90 degrees is naturally not included in these angular ranges showing inclination.

An advantage by this bonded portion row which does not extend in the orthogonal direction XD and is inclined to intersect with the stretchable direction ED becomes clear by comparing with an eighth embodiment illustrated in FIG. 18. That is, in the example illustrated in FIG. 19, a reason for having the advantage is that, for example, the separation interval between the first bonded portions 40 and 40 on the orthogonal direction XD line is considerably larger than that in the eighth embodiment illustrated in FIG. 18.

That is, for example, bonding of the first sheet layer 20A and the second sheet layer 20B at the bonded portions 40 is desirably performed by bonding means by material welding such as heat sealing or ultrasonic sealing.

In the case of continuous production, seal melting by ultrasonic waves is performed between the anvil roll and the ultrasonic horn. However, in order to prevent energy loss, it is important that the ultrasonic horn is in close contact with the sheet throughout entire part of the anvil roll in an axial direction. For this reason, it is necessary to output a large ultrasonic wave in the case of forming a pattern having a large proportion of anvil roll convexes as the row of the bonded portions 40, 40 . . . of FIG. 12 along a generatrix that makes line contact. To this end, when an excessive close force is applied along the generatrix that makes line contact, the load on the facility side is large.

On the other hand, in the case of this example (generally in the case of the inclined arrangement), the proportion of the bonded portions located on the line in the orthogonal direction XD is small, and the stable linear pressure is obtained. Thus, the facility load becomes small, and stable operation can be performed. In addition, in this example, the first bonded portions 40 (and the second bonded portions 42) are inclined, and thus there is an advantage that the pleats excellent in the design property can be formed.

(Non-Stretchable Region)

In the region of the outer body 20 having the elastic sheet stretchable structure 20X, as illustrated in FIG. 7, a non-stretchable region 70 can be provided in addition to the stretchable region 80. The non-stretchable region 70 means that the elongation at elastic limit in the stretchable direction is 120% or less. The elongation at elastic limit of the non-stretchable region 70 is preferably 110% or less, and more preferably 100%. Arrangement of the stretchable region 80 and the non-stretchable region 70 can be appropriately determined. In the case of the outer body 20 of the underpants-type disposable diaper as in the illustrated example, a part overlapping the absorber 13 is a region that does not require extension and contraction. Thus, as in the illustrated example, it is preferable that a part or all of the part overlapping the absorber 13 (desirably including substantially the entire inner/outer fixing region 10B) is set to the non-stretchable region 70. Naturally, the non-stretchable region 70 may be provided from the region overlapping the absorber 13 to the region not overlapping the absorber 13 positioned in the width direction WD or the front-back direction LD thereof, or the non-stretchable region 70 may be provided only in the region not overlapping the absorber 13.

A shape and arrangement of the individual bonded portions 40 in the non-stretchable region 70, and a shape and arrangement of the joint holes 31 in the elastic sheet 30 can be appropriately determined.

In addition, the area ratio of the bonded portions 40 and the area of the individual bonded portions 40 in the non-stretchable region can be appropriately determined. In a normal case, the following ranges are preferable since the area of each of the bonded portions 40 is small and the area ratio of the bonded portions 40 is low, so that the non-stretchable region 70 does not become hard.

Area of each of bonded portions 40: 0.10 to 0.75 mm$^2$ (especially 0.10 to 0.35 mm$^2$)

Area ratio of bonded portions 40: 4 to 13% (especially 5 to 10%)

The non-stretchable region 70 can be formed by arranging the bonded portions 40 densely so that the pleats are not formed by the first sheet layer and the second sheet layer contracting due to the contraction force of the elastic sheet 30. Specific examples of the method of forming the non-stretchable region 70 include those shown in JP 5980355 B2, JP 5918877 B1, JP 5980367 B1, and JP 6049228 B1.

In particular, the non-stretchable region 70 is preferably a region not having a linearly continuous part along the width direction WD due to the presence of the joint holes 31 even though the elastic sheet 30 is continuous in the width direction WD. In this case, even when in a state where the elastic sheet 30 is extended in the width direction WD, the first sheet layer 20A and the second sheet layer 20B are bonded through the joint holes 31 of the elastic sheet 30 at intervals in the width direction WD and the front-back direction LD orthogonal thereto, and the plurality of bonded portions 40 is formed, thereby forming the entire elastic sheet stretchable structure 20X including both the stretchable region 80 and the non-stretchable region 70, the elastic sheet 30 is not linearly continuous along the width direction WD in the non-stretchable region 70. Thus, the contraction force of the elastic sheet 30 hardly acts on the first sheet layer 20A and the second sheet layer 20B, the elasticity is lost, and the elongation at elastic limit is close to 100%.

In such a non-stretchable region 70, the first sheet layer 20A and the second sheet layer 20B are bonded at a plurality of bonded portions 40 arranged at intervals, and the bonded portions 40 are not continuous. Thus, a decrease in flexibility is prevented.

(Bonding Structure of Bonded Portions)

In a case where bonding of the first sheet layer 20A and the second sheet layer 20B in the bonded portions 40 is performed through the joint holes 31 formed in the elastic sheet 30, it is desirable that the first sheet layer 20A and the second sheet layer 20B are not bonded to the elastic sheet 30 except at least between the first sheet layer 20A and the second sheet layer 20B in the bonded portions 40.

Bonding means for bonding the first sheet layer 20A and the second sheet layer 20B at the bonded portions 40 is not particularly limited. For example, bonding of the first sheet layer 20A and the second sheet layer 20B at the bonded portions 40 may be performed by a hot melt adhesive, or by bonding means by material welding such as heat sealing or ultrasonic sealing.

In a case where the first sheet layer 20A and the second sheet layer 20B are bonded through the joint holes 31 of the elastic sheet 30 in the bonded portions 40, as a structure in which the bonded portions 40 are formed by material welding, it is possible to adopt any one of a first welded structure in which the first sheet layer 20A and the second sheet layer 20B are bonded only by a melted and solidified material 20m in a most part or a part of at least one of the first sheet layer 20A and the second sheet layer 20B in the bonded portions 40 (see FIG. 21(a)), a second welded structure in which the first sheet layer 20A and the second sheet layer 20B are bonded only by a melted and solidified material 30m in all, a most part, or a part of the elastic sheet 30 in the bonded portions 40 (see FIG. 21(b)), and a third welded structure in which both of these welded structures are combined (see FIG. 21(c)). However, the second and third welded structures are preferable.

A particularly preferable structure is a structure in which the first sheet layer 20A and the second sheet layer 20B are bonded by the melted and solidified material 20m in a part of the first sheet layer 20A and the second sheet layer 20B and the melted and solidified material 30m in all or a most part of the elastic sheet 30 in the bonded portions 40. Note that in the third welded structure illustrated in FIG. 23(b), the melted and solidified material 30m of the elastic sheet 30 shown in white is seen between melted and solidified materials 20m of the fibers of the first sheet layer 20A or the second sheet layer 20B shown in black. On the other hand, in the first welded structure illustrated in FIG. 23(a), the melted and solidified material of the elastic sheet 30 is not seen between melted and solidified materials 20m of the fibers of the first sheet layer 20A or the second sheet layer 20B.

In the case of bonding the first sheet layer 20A and the second sheet layer 20B using the melted and solidified material 20m in a most part or a part of at least one of the first sheet layer 20A and the second sheet layer 20B as an adhesive as in the first adhesive structure or the third adhesive structure, it is preferable that a part of the first sheet layer 20A and the second sheet layer 20B is not melted since the bonded portions 40 are not hardened.

Note that when the first sheet layer 20A and the second sheet layer 20B are nonwoven fabrics, structures in which a part of the first sheet layer 20A and the second sheet layer 20B does not melt include a structure in which a core (including not only a core of a composite fiber but also a central part of a mono-component fiber) remains and a peripheral part thereof (including not only a sheath of the composite fiber but also a surface layer side part of the mono-component fiber) melts for all the fibers of the bonded portions 40, or a structure in which some fibers do not melt at all and the rest of the fibers melt, or the core remains and the peripheral part thereof melts.

When the first sheet layer 20A and the second sheet layer 20B are bonded using the melted and solidified material 30m of the elastic sheet 30 as an adhesive as in the second welded structure and the third welded structure, the peel strength becomes high. The second welded structure can be manufactured by interposing the elastic sheet 30 between the first sheet layer 20A and the second sheet layer 20B, pressurizing/heating sites corresponding to the bonded portions 40, and melting only the elastic sheet 30 under the condition that a melting point of at least one of the first sheet layer 20A and the second sheet layer 20B is higher than a melting point of the elastic sheet 30 and a heating temperature at the time of forming the bonded portions 40.

On the other hand, the third welded structure can be manufactured by interposing the elastic sheet 30 between the first sheet layer 20A and the second sheet layer 20B, pressurizing/heating sites corresponding to the bonded portions 40, and melting at least one of the first sheet layer 20A and the second sheet layer 20B and the elastic sheet 30 under the condition that a melting point of at least one of the first sheet layer 20A and the second sheet layer 20B is higher than a melting point of the elastic sheet 30.

From this point of view, the elastic sheet 30 preferably has a melting point of about 80 to 145° C., the first sheet layer 20A and the second sheet layer 20B preferably have a melting point of about 85 to 190° C., particularly about 150 to 190° C., and a difference between the melting point of the first sheet layer 20A and the second sheet layer 20B and the melting point of the elastic sheet 30 is preferably about 60 to 90° C. In addition, the heating temperature is preferably set to about 100 to 150° C.

In the second welded structure and the third welded structure, when the first sheet layer 20A and the second sheet layer 20B are nonwoven fabrics, the melted and solidified material 30m of the elastic sheet 30 may penetrate between fibers throughout the entire part of the first sheet layer 20A and the second sheet layer 20B in the thickness direction in the bonded portions 40 as illustrated in FIG. 22(c). However, flexibility of the bonded portions 40 becomes high in a structure in which the material penetrates between the fibers to a middle in the thickness direction as illustrated in FIG. 22(a) or a structure in which the material hardly penetrates between the fibers of the first sheet layer 20A and the second sheet layer 20B as illustrated in FIG. 22(b).

FIG. 24 illustrates an example of an ultrasonic sealing device suitable for forming the second welded structure and the third welded structure. In this ultrasonic sealing device, at the time of forming the bonded portions 40, the first sheet layer 20A, the elastic sheet 30, and the second sheet layer 20B are fed between an anvil roll 60 having protrusion portions 60a formed in a pattern of the bonded portions 40 on an outer surface and an ultrasonic horn 61. In this instance, for example, by making a feed transfer speed of the elastic sheet 30 on the upstream side by a feed drive roll 63 and a nip roll 62 slower than a transfer speed on the downstream side of the anvil roll 60 and the ultrasonic horn 61, the elastic sheet 30 is stretched to a predetermined stretch rate in an MD direction (machine direction, flow direction) along a path from a nip position by the feed drive roll 63 and the nip roll 62 to a sealing position by the anvil roll 60 and the ultrasonic horn 61. The stretch rate of the elastic sheet 30 can be set by selecting a speed difference between the anvil roll 60 and the feed drive roll 63, and can be set to, for example, about 300% to 500%. Reference character 62 denotes the nip roll.

The first sheet layer 20A, the elastic sheet 30, and the second sheet layer 20B fed between the anvil roll 60 and the ultrasonic horn 61 are heated by ultrasonic vibration energy of the ultrasonic horn 61 while being pressed between the protrusion portions 60a and the ultrasonic horn 61 in a state of being stacked in this order, and only the elastic sheet 30 is melted, or at least one of the first sheet layer 20A and the second sheet layer 20B and the elastic sheet 30 are melted, thereby bonding the first sheet layer 20A and the second sheet layer 20B through the joint holes 31 simultaneously with formation of the joint holes 31 in the elastic sheet 30. Therefore, in this case, the area ratio of the bonded portions 40 can be selected by selecting a size, a shape, a separation interval, and an arrangement pattern in a roll length direction and a roll circumferential direction of the protrusion portions 60a of the anvil roll 60.

Even though a reason why the joint holes 31 are formed may not be clear, it is considered that the holes are opened when parts of the elastic sheet 30 corresponding to the protrusion portions 60a of the anvil roll 60 are melted and separated from the surroundings. In this instance, as illustrated in FIGS. 9(a) and 11(a), a part between adjacent joint holes 31 arranged in the stretchable direction ED in the elastic sheet 30 is cut from parts on both sides of the joint holes 31 in the stretchable direction and loses support on both sides in the stretchable direction. Thus, within a range in which continuity in the direction orthogonal to the contraction direction can be maintained, a center side in the direction LD orthogonal to the stretchable direction ED contracts until the center side balances with a center side in the stretchable direction, and the joint holes 31 expand in the stretchable direction ED.

As a constituent material of the first sheet layer 20A and the second sheet layer 20B, any sheet-shaped material can be used without particular limitation. However, it is preferable to use a nonwoven fabric from a viewpoint of air permeability and flexibility. A raw material fiber of the nonwoven fabric is not particularly limited. Examples of the raw material fibers can include synthetic fibers such as polyolefin-based fiber such as polyethylene and polypropylene, polyester-based fiber, and polyamide-based fiber, regenerated fibers such as rayon and cupra, natural fibers such as cotton, mixed fibers and conjugate fibers in which two or more of these are used, and the like. Further, the nonwoven fabric may be manufactured by any processing.

As a method of fiber bonding in the nonwoven fabric, it is possible to adopt any one of chemical means such as an adhesive or a solvent, physical means such as heating, or so-called entanglement. For example, it is possible to adopt a spun lace method, a spun bond method, a thermal bond method, a melt blown method, a needle punch method, an air through method, a point bond method, etc. When the nonwoven fabric is used, a basis weight thereof is preferably set to about 10 to 25 g/m$^2$. Further, a part or all of the first sheet layer 20A and the second sheet layer 20B may be a pair of layers in which a single material is folded back to face each other. For example, as in the illustrated example, in the waist end portions 23, a constituent material located outside may be set to the second sheet layer 20B, the folded part 20C folded back to the internal surface side at a waist opening edge may be set to the first sheet layer 20A, and the elastic sheet 30 may be interposed therebetween. In other parts, a constituent material located inside may be set to the first sheet layer 20A, a constituent material located outside may be set to the second sheet layer 20B, and the elastic sheet 30 may be interposed therebetween. Naturally, the constituent material of the first sheet layer 20A and the constituent material of the second sheet layer 20B may be individually provided over the entire part in the front-back direction LD, and the elastic sheet 30 may be interposed between the constituent material of the first sheet layer 20A and the constituent material of the second sheet layer 20B without folding the constituent materials.

The elastic sheet 30 is not particularly limited, and may be a stretchable nonwoven fabric other than an elastic film as long as the sheet is made of a thermoplastic resin that elastically extends and contracts. In addition, as the elastic sheet 30, it is possible to use not only a non-perforated sheet but also a sheet provided with a plurality of holes or slits for ventilation. In particular, it is preferable that the elastic sheet 30 has a tensile strength of 8 to 25 N/35 mm in the width direction WD (stretchable direction ED and MD direction), a tensile strength of 5 to 20 N/35 mm in the front-back direction LD (direction XD orthogonal to the stretchable direction and CD direction), a tensile elongation of 450 to 1050% in the width direction WD, and a tensile elongation of 450 to 1400% in the front-back direction LD. A thickness of the elastic sheet 30 is not particularly limited, and is preferably about 20 to 40 µm. In addition, an elastic non-woven fabric may be provided on one side or both sides of an elastic film, which may be interposed as the elastic sheet 30 between the first sheet layer 20A and the second sheet layer 20B.

(Design)

As illustrated in FIG. 26(a), a part of the elastic sheet 30 located in the stretchable region 80 is printed with a first design 51 including design elements 51a, and a part of the elastic sheet 30 located in the non-stretchable region 70 is printed with a second design 52 including design elements 52a. The first design 51 and the second design 52 are the same when the stretchable region 80 and the non-stretchable region 70 are at the elongation at elastic limit. In addition, as a matter of course, the first design 51 and the second design 52 are visible from the outside of the outer body 20.

To impart the first design 51 and the second design 52 to the elastic sheet 30, in manufacturing, it is possible to use the elastic sheet 30 in which the first design 51 is preprinted on the part corresponding to the stretchable region 80, and the second design 52 is preprinted on the part corresponding to the non-stretchable region 70. In addition, prior to stretching of the elastic sheet 30 (on the upstream side of the feed drive roll 63 and the nip roll 62 in the manufacturing method of FIG. 24), the first design 51 may be printed in-line on the part of the elastic sheet 30 corresponding to the stretchable region 80, and the second design 52 may be printed on the part corresponding to the non-stretchable region 70. A printing method is not particularly limited, and may be letterpress printing, gravure printing, offset printing, inkjet printing, etc. In order to improve the printability of the elastic sheet 30, it is desirable to perform corona treatment on a printed surface.

The first design 51 may be provided not only on a portion of the part of the elastic sheet 30 located in the stretchable region 80 but also on the entire part of the elastic sheet 30 located in the stretchable region 80. The second design 52 may be provided not only on a portion of the part of the elastic sheet 30 located in the non-stretchable region 70 but also on the entire part of the elastic sheet 30 located in the non-stretchable region 70.

The first design 51 and the second design 52 are not particularly limited and may be, for example, a pattern for decoration (in addition to a polka dot pattern, a floral pattern, etc., a picture and a one-point character are included), function display such as a usage method, a usage assistance, or a size, mark display such as a manufacturer, a product name, or a characteristic function, or a combination of a plurality of these types. The design elements 51a, 52a, and 53a, including a third design 53 described below, are elements constituting a part that can be distinguished from other parts in the designs 51, 52, and 53 and are not particularly limited. For example, the design elements may be various geometric figures (for example, a circle in a polka dot pattern), hieroglyphics (a figure that represents a shape of an object by abstraction (for example, a single flower-shaped figure in a floral pattern), a picture (for example, a picture of a single flower in a floral pattern), a letter, or a combination of a plurality of these types. The design elements 51a, 52a, and 53a may be arranged at intervals, or may be arranged so as to be in contact with other design elements.

Characteristically, as illustrated in FIG. 26 by comparing (a) the spread state (state of being stretched in the width direction to the elongation at elastic limit), (b) the natural length state, and (c) the worn state (the stretch rate in the width direction is within a range of 130 to 170%), a stretchable direction dimension 51x of the design elements 51a of the first design 51 when the stretch rate of the stretchable region 80 is 130% or more (an upper limit is inevitably the elongation at elastic limit) is set to 80% or more, particularly 90% of the stretchable direction dimension 51x of the design elements of the first design 51 when the stretchable region 80 is at the elongation at elastic limit. This setting can be achieved by suppressing a difference between the stretch rate in the worn state and the elongation at elastic limit to some extent. To this end, the above-mentioned arrangement examples 3 to 11 are particularly suitable.

Note that as described above, "the same" with respect to the first design 51 and the second design 52 means that the design elements 51a and 52a have the same dimensions, shapes, orientations, arrangements, etc. However, it is natural that the areas of the designs 51 and 52, the number of design elements 51a and 52a that change depending on the area, how the design elements 51a and 52a are discontinued, or missing may be different.

In this disposable wearable article, the first design 51 and the second design 52 are the same when the stretchable region 80 and the non-stretchable region 70 are at the elongation at elastic limit. This description merely means that uniform printing is applied to the part corresponding to the stretchable region 80 and the part corresponding to the non-stretchable region 70 in the elastic sheet 30. In addition, in this disposable wearable article, the stretchable direction dimension 51x of the design elements 51a of the first design 51 when the stretch rate of the stretchable region 80 is 130% or more, that is, in a general worn state is 80% or more, particularly 90% or more of the stretchable direction dimension 51x of the design elements 51a of the first design 51 when the stretchable region 80 is at the elongation at elastic limit. For this reason, there is little difference in appearance between the designs 51 and 52 in the stretchable region 80 and the non-stretchable region 70 during wearing. For example, when the first design 51 and the second design 52 are printed on the elastic sheet 30 to obtain a normal state in which the first design 51 and the second design 52 at the elongation at elastic limit are not deformed, a particularly preferable appearance is obtained during wearing.

In general, the disposable wearable article does not frequently have a stretchable structure as a whole. This description is similarly applied to the case of adopting the elastic sheet stretchable structure 20X. Specifically, in the example illustrated in FIG. 1, etc., the elastic sheet stretchable structure 20X is not provided in a middle of the intermediate portion L of the outer body 20 in the front-back direction LD. In such a case, to add a design to a wider range, as in an example illustrated in FIGS. 27 and 28, it is preferable to provide the third design 53 including the design elements 53a and 53b to a non-stretchable sheet 19 other than the elastic sheet 30 extending from the non-stretchable region 70 to a region not having the elastic sheet stretchable structure 20X. The non-stretchable sheet 19 is not particularly limited as long as the third design 53 printed thereof is visible from the outer surface. In the underpants-type disposable diaper of the illustrated example, the non-stretchable sheet 19 may be a sheet (for example, the liquid impervious sheet 12 as in the illustrated example) closer to the outer side in the inner body 10, and it is desirable that the third design 53 is printed on an outer surface thereof.

In the case of providing the third design 53, to enhance integrity of the design, the third design 53 preferably includes design elements which are the same as the design elements of the first design 51 when the stretchable region 80 and the non-stretchable region 70 are at the elongation at elastic limit. In this way, the difference in appearance between the first design 51 and the third design 53 decreases in the worn state. Note that as described above, "the same" design elements with respect to the first design 51 and the third design 53 means that dimensions and shapes are the same, and colors and directions may be different.

As long as third design 53 includes design elements 53a which are the same as the design elements 51a of the first design 51 described above, the third design 53 may include only the same design elements 53a, or may include design elements 53b in which one or both designs are different from the other design.

In the case of providing the second design 52 and the third design 53 described above, in the non-stretchable region 70, there is concern that the design elements 52a of the second design 52 of the elastic sheet 30 and the design elements 53a and 53b of the third design 53 of the non-stretchable sheet 19 may overlap with each other, resulting in a cluttered appearance. Therefore, as illustrated in FIG. 28, it is proposed that the third design 53 is obtained by arranging the design elements 53a and 53b at intervals, a minimum value of a stretchable direction interval 53d between the design elements 53a and 53b arranged side by side in the stretchable direction in the third design 53 is set to be larger than (for example, about 1.5 to 7 times, in particular about 2 to 5 times) a minimum value of a stretchable direction dimension 52x of the design elements 52a of the second design 52, and a minimum value of an orthogonal direction XD interval 53e of the design elements 53a and 53b arranged side by side in the orthogonal direction XD orthogonal to the stretchable direction in the third design 53 is set to be larger than (for example, about 1.5 to 7 times, in particular about 2 to 5 times) a minimum value of an orthogonal direction XD dimension 52y of the design elements 52a of the second design 52. In this way, when the intervals 53d and 53e of the design elements 53a and 53b of the third design 53 are sufficiently sparse with respect to the sizes 52x and 52y of the design elements 52a of the second design 52, the design elements 52a, 53a, and 53b rarely overlap each other, and clutter in appearance can be suppressed when compared to the opposite case. In the illustrated example, the intervals 53d and 53e of the design elements 53a and 53b of the third design 53 are set to be larger than the sizes 52x and 52y of the design elements 52a of the second design 52. However, on the contrary, the intervals 52d and 52e of the design elements 52a of the second design 52 may be set to be larger than the sizes 53x and 53y of the design elements 53a and 53b of the third design 53.

The dimensions and intervals of the design elements 51a, 52a, 53a, and 53b may be set as appropriate, and one example is as follows. Note that the following dimensions mean values when the stretchable region 80 and the non-stretchable region 70 are at the elongation at elastic limit (spread state).

(First Design·Second Design)
  stretchable direction dimensions 51x and 52x of design elements: 5 to 25 mm, especially 10 to 20 mm
  Orthogonal direction dimensions 51y and 52y of design elements: 5 to 25 mm, especially 10 to 20 mm
  stretchable direction intervals 51d and 52d of design elements: 0 to 100 mm, especially 20 to 50 mm
  Orthogonal direction intervals 51e and 52e of design elements: 0 to 100 mm, especially 20 to 50 mm
(Third Design)
  stretchable direction dimension 53x of design element: 5 to 25 mm, especially 10 to 20 mm
  Orthogonal direction dimension 53y of design element: 5 to 25 mm, especially 10 to 20 mm
  stretchable direction interval 53d of design element: 0 to 150 mm, especially 50 to 100 mm
  Orthogonal direction interval 53e of design element: 0 to 150 mm, especially 50 to 100 mm Description of Terms Used Herein The following terms in the specification have the following meanings unless otherwise specified in the specification.

"Front body" and "back body" mean a front side part and a back side part, respectively, with a center of the underpants-type disposable diaper in the front-back direction as a boundary. In addition, the crotch portion means a front-back direction range including the center of the underpants-type disposable diaper in the front-back direction, and when the absorber has a narrowing portion, the crotch portion means a front-back direction range of a part having the narrowing portion.

"Front-back direction" means a direction (longitudinal direction) indicated by the reference character LD in the figure, "width direction" means a direction (right-left direction) indicated by WD in the figure, and the front-back direction and the width direction are orthogonal to each other.

"Elongation at elastic limit" means elongation of an elastic limit in the stretchable direction ED (in other words, a state where the first sheet layer and the second sheet layer are completely spread), and expresses a length at the elastic limit as a percentage when the natural length is 100%.

"Area ratio" means a ratio of a target part to a unit area, and expresses a total area of target parts (for example, the bonded portions 40, openings of the joint holes 31, and vent holes) in a target region (for example, the stretchable region 80 and the non-stretchable region 70) as a percentage by dividing the total area by the area of the target region. In particular, "area ratio" in a region having the stretchable structure means an area ratio in a state of stretching to the elastic limit in the stretchable direction ED. When a plurality of target parts is provided at intervals, it is desirable to obtain an area ratio by setting a target region having a size at which 10 or more target parts are included.

"Stretch rate" means the value when the natural length is taken as 100%. For example, a stretch rate of 200% is synonymous with a stretch magnification of 2 times.

"Basis weight" is measured as follows. After the sample or test piece is preliminary dried, it is allowed to stand in a test room or apparatus under normal conditions (the test location is at a temperature: 23±1° C., relative humidity: 50±2%) until the constant mass. The preliminary drying is to make the sample or test piece be constant mass in an environment of a temperature of 100° C. Note that the fibers of an official moisture regain of 0.0% do not need preliminary drying. From a test piece having a constant weight, a sample having a dimension of 100 mm×100 mm is cut out using a template for sampling (100 mm×100 mm). The sample is weighed and the weight is multiplied by 100 into the weight per one square meter. The resulting value is defined as the basis weight.

"Thickness" of the absorber is measured using a thickness measuring instrument of OZAKI MFG. CO., LTD. (PEACOCK, digital type, model FFD-7 (measurement range 0 to 20 mm)) by making the sample and the thickness measuring instrument horizontal.

"Thickness" other than the above thickness is automatically measured using an automatic thickness measuring instrument (KES-G5 Handy Compression Measurement Program) under the conditions of load: 0.098 N/cm$^2$ and pressurized area: 2 cm$^2$.

"Tensile strength" and "Tensile elongation (elongation at break)" mean values measured by setting an initial chuck interval (distance between marked lines) to 50 mm, and a pulling speed to 300 mm/min in accordance with JIS K7127:1999 "Plastic—Test method for tensile properties" except that a test piece has a rectangular shape having a width of 35 mm×a length of 80 mm. As a tensile testing machine, for example, it is possible to use AUTOGRAPH AGS-G100N manufactured by SHIMADZU CORPORATION.

"Extension stress" means a tensile stress (N/35 mm) measured at the time of stretching within an elastic region by a tensile test in which an initial chuck interval (distance between marked lines) is set to 50 mm, and a pulling speed is set to 300 mm/min in accordance with JIS K7127:1999 "Plastic—Test method for tensile properties", and a degree of stretching can be appropriately determined depending on the test subject. It is preferable to form the test piece having a width of 35 mm in a rectangular shape having a length of 80 mm or more. However, when a test piece having a width of 35 mm may not be cut out, a test piece having a width that allows cutting out is prepared, and a measured value is set to a value converted into the width of 35 mm. In addition, even in a case where the target region is small and sufficient test pieces may not be collected, when the magnitude of the extension stress is compared, at least comparison can be performed using appropriately small test pieces as long as the test pieces have the same dimensions. As a tensile testing machine, for example, it is possible to use AUTOGRAPH AGS-G100N manufactured by SHIMADZU CORPORATION.

"Spread state" means a flatly spread state without contraction or slack.

The dimension of each part means the dimension in the spread state, not the natural length state, unless otherwise specified. In particular, the dimensions of the bonded portions are dimensions in a state of being spread to the limit (state before the first sheet layer and the second sheet layer are broken), and substantially coincide with the bonded portion pattern dimensions in the anvil roll.

When environmental conditions in tests and measurements are not described, the tests and measurements shall be carried out in a test room or apparatus under normal conditions (the test location is at a temperature: 23±1° C., relative humidity: 50±2%).

INDUSTRIAL APPLICABILITY

As long as the stretchable region to which the elastic sheet stretchable structure can be applied is included, the invention can be used for general disposable wearable articles such as various disposable diapers of tape type, pad type, etc., sanitary napkins, and disposable wearable articles for swimming and water play in addition to the underpants-type disposable diaper as in the example.

REFERENCE SIGNS LIST

10 INNER BODY
10B INNER/OUTER FIXING REGION
11 TOP SHEET
12 LIQUID IMPERVIOUS SHEET
13 ABSORBER
13N NARROWING PART
14 WRAPPING SHEET
17 NON-ABSORBER SIDE PORTION
19 NON-STRETCHABLE SHEET
20 OUTER BODY
20A FIRST SHEET LAYER
20B SECOND SHEET LAYER
20C FOLDED PART
20X ELASTIC SHEET STRETCHABLE STRUCTURE
21 SIDE SEAL PORTION
23 WAIST END PORTION
24 WAIST PORTION ELASTIC MEMBER
25F, 25f CONTRACTION WRINKLE
29 AROUND-LEG LINE
30 ELASTIC SHEET
31 JOINT HOLE
33 VENT HOLE
40, 40A, 40B BONDED PORTION (FIRST BONDED PORTION)
41 SECOND BONDED PORTION
42 THIRD BONDED PORTION
43 FOURTH BONDED PORTION
51 FIRST DESIGN
52 SECOND DESIGN
53 THIRD DESIGN
70 NON-STRETCHABLE REGION
80 STRETCHABLE REGION
82 EDGE PORTION STRETCHABLE REGION
90 THREE-DIMENSIONAL GATHER
93 FALLEN PORTION
94 FREE PART
95 GATHER SHEET
96 GATHER ELASTIC MEMBER
B BACK BODY
ED STRETCHABLE DIRECTION (WIDTH DIRECTION)
F FRONT BODY
L INTERMEDIATE PORTION
XD ORTHOGONAL DIRECTION
LD FRONT-BACK DIRECTION
T LOWER TORSO PORTION
sf SMALL PLEAT
bf LARGE PLEAT
Px SEPARATION DISTANCE
Py SEPARATION DISTANCE
E1 FIRST STRETCHABLE REGION
E2 SECOND STRETCHABLE REGION
E3 INTERMEDIATE REGION

The invention claimed is:
1. A disposable wearable article having an elastic sheet stretchable structure in which an elastic sheet is stacked between a first sheet layer and a second sheet layer, and the first sheet layer and the second sheet layer are bonded through joint holes penetrating the elastic sheet or with the elastic sheet interposed therebetween at a plurality of bonded portions arranged at intervals,
  wherein a region having the elastic sheet stretchable structure has a stretchable region which contracts in a stretchable direction by a contraction force of the elastic sheet and is stretchable in the stretchable direction, and a non-stretchable region,
  a part of the elastic sheet located in the stretchable region is printed with a first design including design elements,
  a part of the elastic sheet located in the non-stretchable region is printed with a second design including design elements,
  the first design and the second design are the same when the stretchable region and the non-stretchable region are at an elongation at elastic limit, and
  a stretchable direction dimension of the design elements of the first design when a stretch rate of the stretchable region is 130% or more is 80% or more of a stretchable direction dimension of the design elements of the first design when the stretchable region is at the elongation at elastic limit.

2. The disposable wearable article according to claim 1, comprising:
  a region having the elastic sheet stretchable structure and a region not having the elastic sheet stretchable structure which is continuous with the region having the elastic sheet stretchable structure; and
  a non-stretchable sheet other than the elastic sheet extending from the non-stretchable region to the region not having the elastic sheet stretchable structure,
  wherein the non-stretchable sheet is printed with a third design including a design element, and
  the third design includes design elements which are the same as the design elements of the first design when the stretchable region and the non-stretchable region are at the elongation at elastic limit.

3. The disposable wearable article according to claim 2,
  wherein design elements are arranged at intervals in at least one of the second design and the third design,
  at least parts of the second design and the third design overlap each other,
  a minimum value of a stretchable direction interval of design elements arranged in the stretchable direction in one of the second and the third designs is larger than a minimum value of a stretchable direction dimension of design elements in the other of the second and the third design, and
  a minimum value of an orthogonal direction interval of design elements arranged in an orthogonal direction orthogonal to the stretchable direction in the one of the second and the third designs is larger than a minimum value of an orthogonal direction dimension of design elements in the other of the second and the third designs.

4. The disposable wearable article according to claim 2,
  wherein the disposable wearable article is an underpants-type disposable wearable article comprising:
  an integral outer body covering a front body and a back body or an outer body separately provided to the front body and the back body;
  an inner body attached to an intermediate portion of the outer body in a width direction and extending to both front and back sides of a crotch portion;
  side seal portions obtained by bonding both side portions of the outer body in the front body and both side portions of the outer body in the back body, respectively;
  a waist opening;
  a pair of right and left leg openings; and
  an absorber included in the inner body and extending to the both front and back sides of the crotch portion,
  wherein the outer body in at least one of the front body and the back body has an absorber region defined as a front-back direction range overlapping the absorber, and the elastic sheet stretchable structure is provided over at least a width direction range corresponding to a part between the side seal portions in the absorber region so that a stretchable direction thereof becomes the width direction, and
  in the absorber region, an intermediate portion in the width direction is the non-stretchable region, and a width direction range corresponding to a part between the non-stretchable region and the side seal portions is the stretchable region.

5. The disposable wearable article according to claim 3,
  wherein the disposable wearable article is an underpants-type disposable wearable article comprising:
  an integral outer body covering a front body and a back body or an outer body separately provided to the front body and the back body;
  an inner body attached to an intermediate portion of the outer body in a width direction and extending to both front and back sides of a crotch portion;
  side seal portions obtained by bonding both side portions of the outer body in the front body and both side portions of the outer body in the back body, respectively;
  a waist opening;
  a pair of right and left leg openings; and
  an absorber included in the inner body and extending to the both front and back sides of the crotch portion,
  wherein the outer body in at least one of the front body and the back body has an absorber region defined as a front-back direction range overlapping the absorber, and the elastic sheet stretchable structure is provided over at least a width direction range corresponding to a part between the side seal portions in the absorber region so that a stretchable direction thereof becomes the width direction, and
  in the absorber region, an intermediate portion in the width direction is the non-stretchable region, and a width direction range corresponding to a part between the non-stretchable region and the side seal portions is the stretchable region.

6. The disposable wearable article according to claim 1,
  wherein the disposable wearable article is an underpants-type disposable wearable article comprising:
  an integral outer body covering a front body and a back body or an outer body separately provided to the front body and the back body;
  an inner body attached to an intermediate portion of the outer body in a width direction and extending to both front and back sides of a crotch portion;
  side seal portions obtained by bonding both side portions of the outer body in the front body and both side portions of the outer body in the back body, respectively;
  a waist opening;
  a pair of right and left leg openings; and
  an absorber included in the inner body and extending to the both front and back sides of the crotch portion,
  wherein the outer body in at least one of the front body and the back body has an absorber region defined as a front-back direction range overlapping the absorber, and the elastic sheet stretchable structure is provided over at least a width direction range corresponding to a part between the side seal portions in the absorber region so that a stretchable direction thereof becomes the width direction, and in the absorber region, an intermediate portion in the width direction is the non-stretchable region, and a width direction range corresponding to a part between the non-stretchable region and the side seal portions is the stretchable region.

* * * * *